United States Patent [19]

McNichols et al.

[11] Patent Number: 6,149,755
[45] Date of Patent: Nov. 21, 2000

[54] MACHINE AND PROCESS FOR PLACING DISCRETE COMPONENTS ON A MOVING WEB WITH VELOCITY MATCHED PLACEMENT AND INTEGRAL BONDING

[75] Inventors: Patrick Sean McNichols, Hortonville; Gary Mack Reynolds; James Bennington Stopher, both of Neenah, all of Wis.

[73] Assignee: Kimberly-Clark Worldwide, Inc., Neenah, Wis.

[21] Appl. No.: 09/222,095

[22] Filed: Dec. 29, 1998

[51] Int. Cl.$^7$ ........................................... B32B 31/00
[52] U.S. Cl. ................... 156/264; 156/73.1; 156/285; 156/519; 156/580.2; 156/582
[58] Field of Search ................... 156/73.1, 256, 156/264, 285, 516, 517, 519, 553, 555, 580.1, 580.2, 582

[56] References Cited

U.S. PATENT DOCUMENTS

| | | | |
|---|---|---|---|
| 3,879,246 | 4/1975 | Walker | 156/265 |
| 4,642,150 | 2/1987 | Stemmler | 156/164 |
| 4,713,132 | 12/1987 | Abel et al. | 156/73.1 |
| 4,726,876 | 2/1988 | Tomsovic, Jr. | 156/552 |
| 4,767,487 | 8/1988 | Tomsovic, Jr. | 156/256 |
| 4,795,510 | 1/1989 | Wittrock et al. | 156/64 |
| 5,021,111 | 6/1991 | Swenson | 156/264 |
| 5,104,116 | 4/1992 | Pohjola | 271/185 |
| 5,224,405 | 7/1993 | Pohjola | 83/24 |
| 5,286,317 | 2/1994 | Treat et al. | 156/64 |
| 5,380,381 | 1/1995 | Otruba | 156/64 |
| 5,407,507 | 4/1995 | Ball | 156/163 |
| 5,413,651 | 5/1995 | Otruba | 156/64 |
| 5,415,716 | 5/1995 | Kendall | 156/256 |
| 5,540,796 | 7/1996 | Fries | 156/164 |
| 5,556,504 | 9/1996 | Rajala et al. | 156/519 |
| 5,707,470 | 1/1998 | Rajala et al. | 156/73.2 |
| 5,711,847 | 1/1998 | Rajala et al. | 156/580.2 |
| 5,714,256 | 2/1998 | DeLucia et al. | 428/373 |
| 5,755,902 | 5/1998 | Reynolds | 156/73.1 |
| 5,771,524 | 6/1998 | Woods et al. | 15/209.1 |
| 6,022,431 | 2/2000 | Blenke et al. | 156/73.1 |
| 6,036,805 | 2/2000 | McNichols et al. | 156/227 |
| 7,863,542 | 9/1989 | Oshefsky et al. | 156/160 |

*Primary Examiner*—James Sells
*Attorney, Agent, or Firm*—Jerry F. Janssen; Thomas D. Wilhelm

[57] ABSTRACT

The present invention provides a combination roller, a machine and process for cutting workpieces from a web moving at a first speed and depositing them on and bonding them to a substrate web moving at a second speed with the functions of cutting, transferring, and bonding all carried out on a single roller. The reduction in roller mass achieved by this roller and machine design permits driving the combination roller at variable speeds by means of a servomotor and servomotor controller. The resulting machine permits electronic rather than machine grade changes as the machine and process are used to produce products having different configurations.

55 Claims, 16 Drawing Sheets

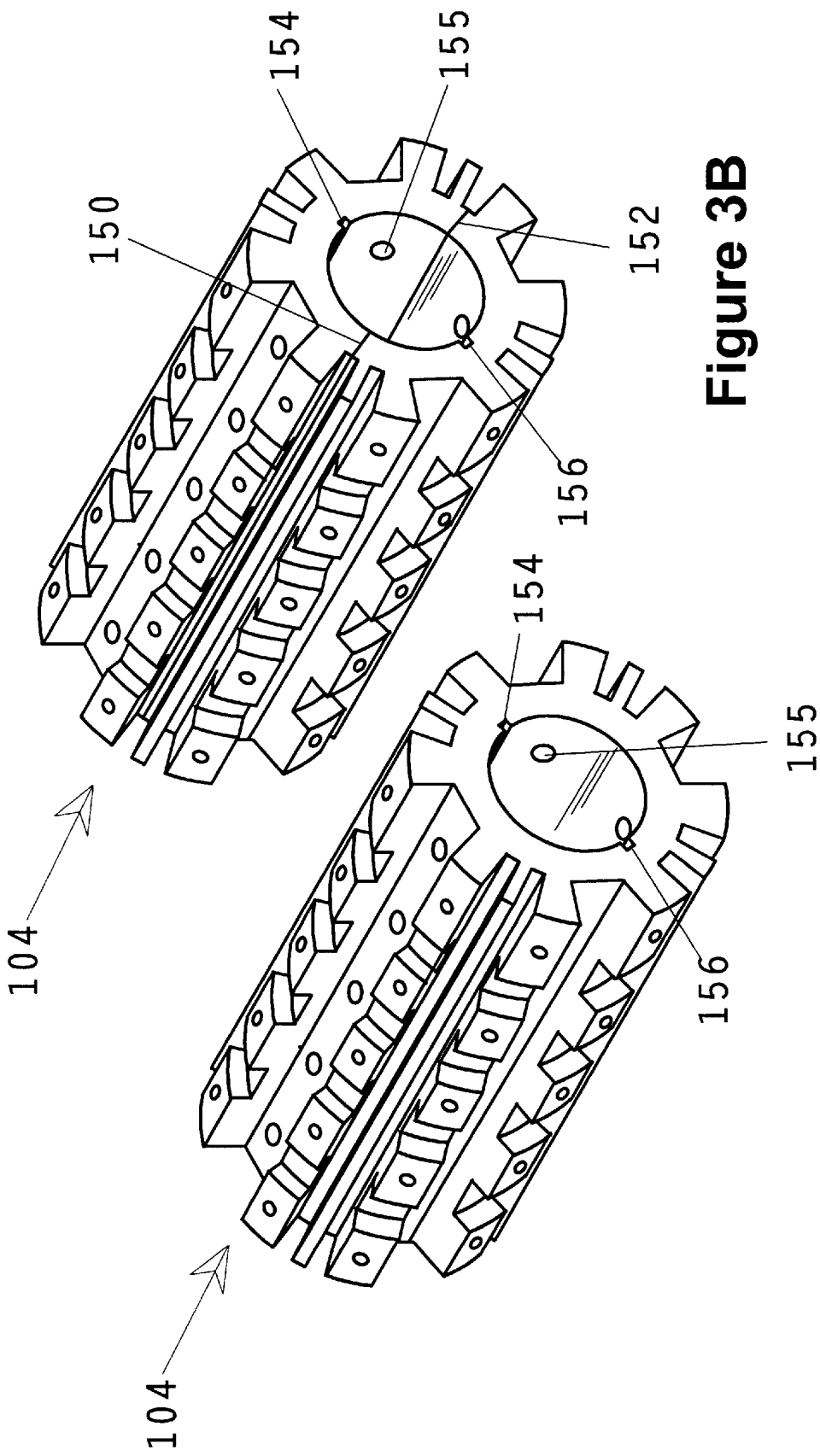

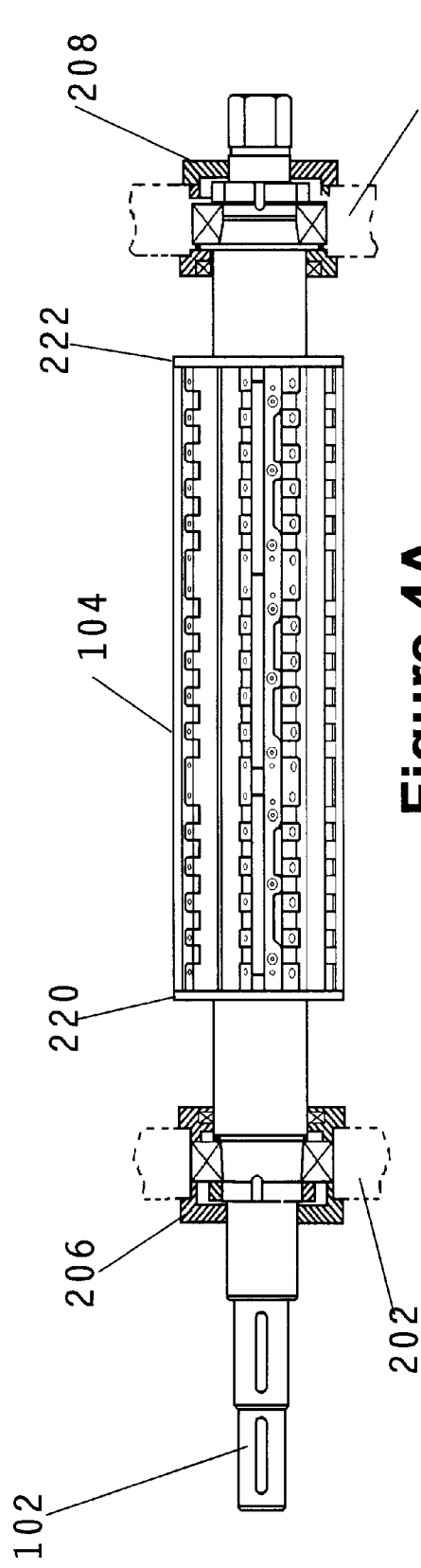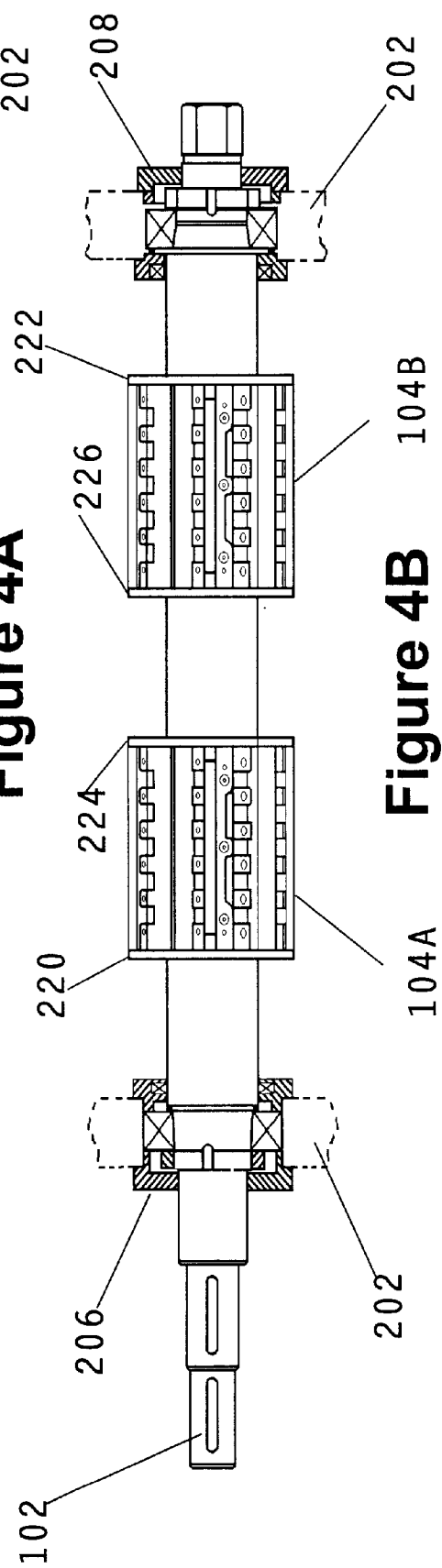
Figure 4A
Figure 4B

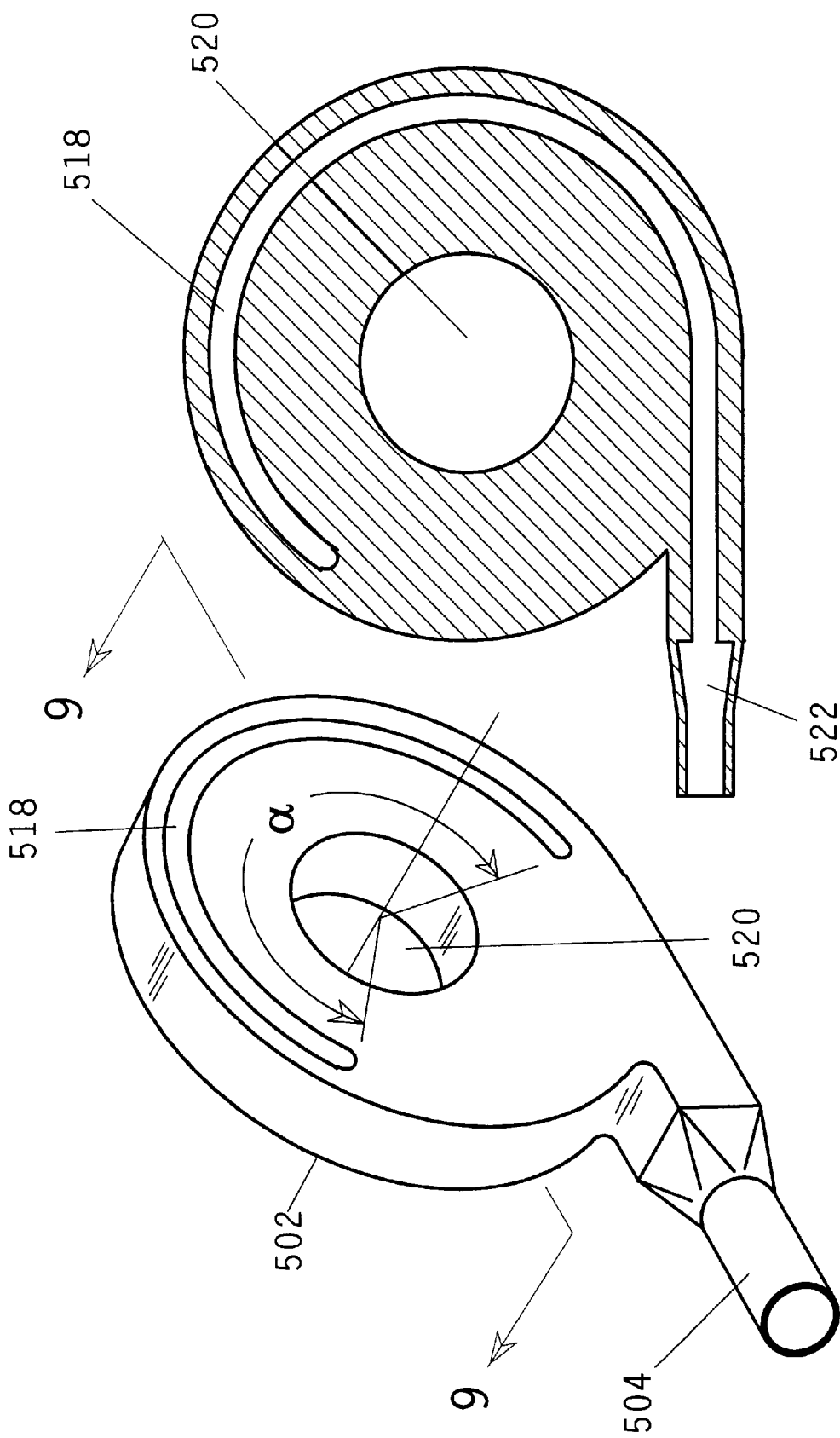

MACHINE AND PROCESS FOR PLACING DISCRETE COMPONENTS ON A MOVING WEB WITH VELOCITY MATCHED PLACEMENT AND INTEGRAL BONDING

TECHNICAL FIELD

The present invention relates to a method and apparatus for receiving discrete parts of a workpiece traveling at one speed and applying and bonding the parts to a web of material moving at a different speed. More particularly, the invention concerns a method and apparatus for cutting, transporting, and bonding on a single roller, discrete parts from a web of material moving at one speed to a web of material moving at a different speed.

BACKGROUND OF THE INVENTION

Articles such as infant diapers, adult continence diapers, feminine napkins and the like have been manufactured generally by processes where discrete parts or components of the article are deposited on a continuously moving product web. Often, the speed with which the parts or components are produced and fed into the process is not the same as the speed of advance of the product web itself. In such cases, the speed of production and/or deposition of the component parts on the moving web must be varied to match the speed of the product web to properly match the parts to the moving web without adversely affecting the process or the quality of the finished article.

Several methods for changing the speed of a part or component of material for deposition on a continuously moving web are known in the art. One method, disclosed in U.S. Pat. Nos. 4,726,876 and 4,767,487 to Tomsovic, Jr. employs rollers segmented into sections which are inwardly and outwardly moveable in a direction radial to their direction of rotation. As the roller rotates, the segments are driven by cam actuating or gearing means to move inwardly and outwardly changing the linear surface speed of the roller segments as the roller rotates through each revolution.

U.S. Pat. No. 5,021,111 to Swenson discloses an apparatus in which an advancing web of material is fed from a slow moving feed roll to a faster moving roller which slips against the web. As components are cut from the slower moving web they are free to move with the faster moving "slip" roller from which they are then transferred to a web moving at the same speed.

Another method utilizes festoons to reduce the speed of the moving web to which the parts or components are to be applied. The continuously moving web is temporarily slowed to the speed of the component parts to be deposited, with the excess portion of the continuously moving web gathering in festoons. While the continuously moving web is slowed to match the speed of the component parts, the parts are transferred to the web and the speed of the web is then accelerated to gather the festoons prior to the next cycle.

Another method disclosed, for example, in U.S. Pat. No. 5,556,504 to Rajala, et al. employs independent segments of a cylindrical surface which comprise a portion of an arc of the circumference of the cylindrical surface. The individual segments are attached to separate concentric shafts and are free to move independently. Each arc surface moves, for a fraction of each rotation, at one speed to receive a workpiece component and then accelerates forward through an angle of rotation to transfer the component to a faster moving web.

U.S. Pat. No. 5,415,716 discloses a machine in which a first web of material is fed from a slower moving feed roller through a system of dancer rollers to a pair of pinch rollers which move the web at a faster speed.

The use of electronically controlled servomotors to control and vary the velocity of various machine roller components is known in the label-making art as illustrated, for example, in U.S. Pat. Nos. 5,380,381 and 5,413,651 to Otruba. Several patents have suggested the use of servomotors for controlling the speed of rollers in machines employed in the fabrication of infant and adult incontinence diapers, feminine care products, and the like. However, the implementation of such a suggestion has faced a number of drawbacks.

Generally, the mass of rollers required in machines for fabricating such articles presents obstacles to the use of servomotors as the driving means. The rapid acceleration/deceleration of massive rollers is beyond the long-term capability of commercially available servomotors. As a result, it has been typical in prior art machines to use mechanical means such as those described above or variable gearing arrangements to meet the demands of the heavy duty cycle imposed by massive machine rollers.

The use of servomotor drive means is also problematic when ultrasonic bonding is used as the means for bonding the discreet components to the moving web. Ultrasonic bonding is a preferable form of bonding components of diapers and feminine care products because it avoids the use of chemical adhesives with their attendant machine drawbacks. However, in machines employing ultrasonic bonding the anvil opposing the ultrasonic horn must be of a mass equal to or greater than the mass of the horn itself to prevent the resonant coupling of the anvil to the horn. This generally imposes a lower limit on the mass of anvil rollers which can be employed with ultrasonic bonding.

Typically in machines in which ultrasonic bonding is employed, the bonding horn(s) and its (their) opposed anvils are placed downstream from the rollers which cut the discrete workpiece components and mate them to the advancing web. This solves one problem, but introduces a second. The mass of the cutting and placing rollers can be lowered to enable driving the rollers by a servomotor, but the separation of the cutting and placing steps from the bonding step becomes problematic. In circumstances where the placement of workpiece components on the advancing web must be maintained with precision, any movement of the component between the placing and bonding steps leads to unacceptable product.

There is thus a need in the industry for a machine and process for cutting, and placing workpiece components from a web moving at one speed onto a receiving web moving at a different speed which permits the integration of the desirable aspects of servomotor control of machine components, while providing for precise registration and ultrasonic bonding of workpiece components.

SUMMARY OF THE INVENTION

These and other advantages are achieved by the present invention which to provides, in its principal embodiment a combination roller having a length and an outer working surface, and a central shaft portion having a length and an outer surface, and a body portion having a length and an outer surface. The combination roller has integral elements of a) a cutting anvil apparatus for engaging the cutting edge of a rotary cutter disposed in cooperative working relationship with the combination roller; b) a vacuum transfer apparatus for receiving and holding a first uncut web of workpieces to the working surface of the combination roller for cutting the first web into discrete workpieces between the cutting edge of the cooperative rotary cutter and the cutting bar anvil and for holding the discrete workpieces to the working surface and transferring the discrete workpieces to a second substrate web; and c) an ultrasonic bonding anvil apparatus for cooperating with the outer working surface of a rotary ultrasonic horn to thereby create bonds bonding the cut discrete workpieces to the second substrate web.

In an alternative embodiment, the present invention provides a machine for cutting discrete workpieces from a first web of uncut workpieces moving at a first speed and transferring and bonding the cut workpieces to a second substrate web of material moving at a second speed. The machine comprises a) a first supply apparatus delivering an uncut web of workpieces at a first component web speed; b) a second supply apparatus delivering a second substrate web of material at a second substrate web speed; c) at least one vacuum commutator; d) at least one rotary ultrasonic horn having an outer working surface; e) a rotary cutter having a length, and having a cutting edge disposed along at least a portion of its length; f) a combination roller having a second outer working surface being disposed in working relationship with the rotary cutter and with the outer working surface of the at least one rotary ultrasonic horn. The combination roller has the integrated elements of i) a cutting bar anvil apparatus for engaging the cutting edge of the rotary cutter during rotation of the rotary cutter and the combination roller, ii) a vacuum transfer apparatus communicating with the at least one vacuum commutator for receiving and holding the first uncut web of workpieces to the working surface of the combination roller for cutting of said first web into discrete workpieces between the cutting edge of the rotary cutter and the cutting bar anvil and for holding the cut discrete workpieces to the working surface and transferring them to the second substrate web; and iii) an ultrasonic bonding anvil apparatus cooperating with the outer working surface of the at least one rotary ultrasonic horn to create bonds bonding the cut discrete workpieces to the second substrate web.

The combination roller and rotary cutter of the machine are driven by a variable speed drive apparatus which drives the rotary cutter and the combination roller at the first component web speed for a first portion of each rotation of the rotary cutter and combination roller at the second substrate web speed for a second portion of each rotation of the rotary cutter and combination roller.

The machine of the present invention thus integrates the functions of cutting the discrete workplace components, transferring them to a receiving substrate web, and bonding them to that substrate web into the functions of two main machine elements: a combination roller and a rotary cutter. The term "combination roller" is used to describe the roller of the machine which combines the functions typically found three separate rollers in prior art machines: cutter anvil roller, vacuum transfer roller, and bonding anvil roller.

In a third embodiment, the invention provides a process for cutting discrete workpieces from a first uncut workpiece web moving at a first workpiece web speed and transferring and bonding the cut discrete workpieces to a substrate web moving at a second substrate web speed. The process comprises carrying out on a single roller the steps of a) receiving on the roller a first uncut workpiece web and cutting discrete workpieces from that first uncut web on the roller while the roller is moving during a first fraction of its rotation at the speed of the first workpiece web and holding the cut discrete workpieces to the roller by vacuum means; b) changing the speed of the roller and discrete workpieces to match the speed of the second substrate web during a second fraction of rotation of the roller; c) transferring said discrete workpieces to the second substrate web and bonding the discrete workpieces to the substrate web while the roller is moving for a third fraction of its rotation at the second substrate web speed; and changing the speed of the roller to approach the speed of the first workpiece web during a fourth fraction of rotation of the roller.

By thus considerably shortening the length of the path between the cutting of the discrete workpiece components and the placing and bonding of the cut components on and to the substrate web, the machine of the present invention provides improved precision of component placement on the substrate web.

Moreover, by consolidating the functions typically provided by three separate rollers into a single roller, the machine of the present invention substantially reduces the mass of machine parts which must be driven at variable speeds thus permitting the use, in a particularly preferred embodiment, of a servomotor and servomotor controller. This permits so-called "electronic grade changes" when the machine is shifted from one product to another, rather than requiring massive re-tooling of the machine.

These advantages and features of the invention are made clear by reference to the following detailed description of the invention and the accompanying Drawing Figures which are a part of this disclosure.

BRIEF DESCRIPTION OF THE DRAWING FIGURES

In the drawing:

FIGS. 3A and 3B are perspective views of one-piece and split, two-piece body portions, respectively, of the combination roller of FIG. 1.

FIGS. 4A and 4B depict alternative embodiments of the shaft and body portions of the combination roller of FIG. 1.

FIG. 8 is a perspective view of a vacuum commutator of the machine sub-assembly shown in FIGS. 5–7.

FIG. 9 is a cross-sectional view of the vacuum commutator of FIG. 8, taken along cut line 9—9.

DETAILED DESCRIPTION

Figure 1:
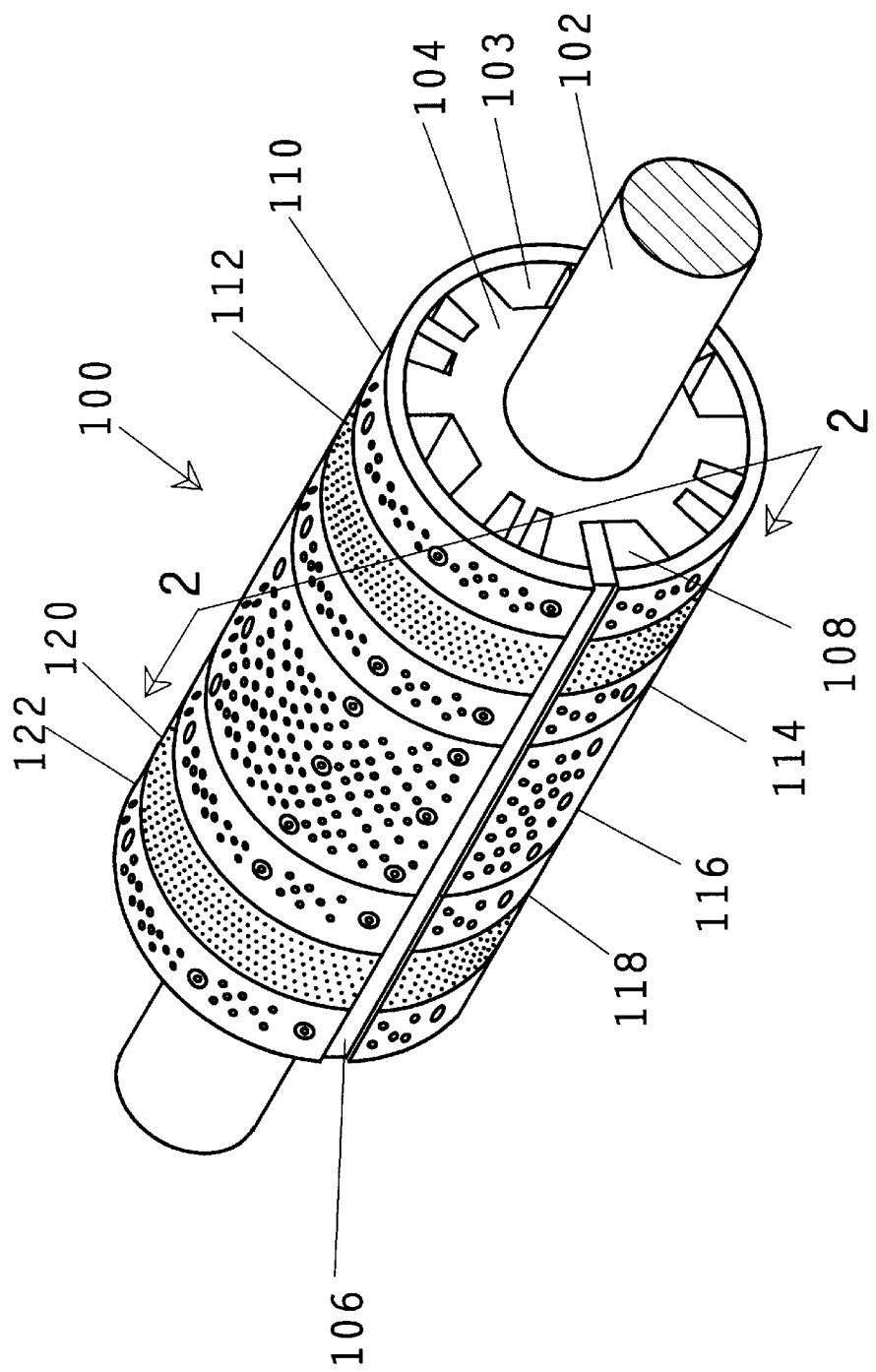
FIG. 1 is a perspective view of one embodiment of a combination roller of the present invention.

A combination roller of one embodiment of the invention is depicted in FIG. 1 where the roller is shown as 100. The roller comprises a shaft portion 102 and a body portion 104. In the embodiment depicted in FIG. 1, ultrasonic bonding anvil shoes 112 and 120 are shown flanked by ultrasonic bonding anvil hold-down shoes 110, 114, 118 and 122. In a manner described in further detail below, the ultrasonic bonding anvil hold-down shoes 110, 114, 118 and 122 are bolted or otherwise fastened to the body portion 104 of the combination roller and retain the ultrasonic bonding anvil shoes 112 and 120 to the roller body portion.

Figure 2:
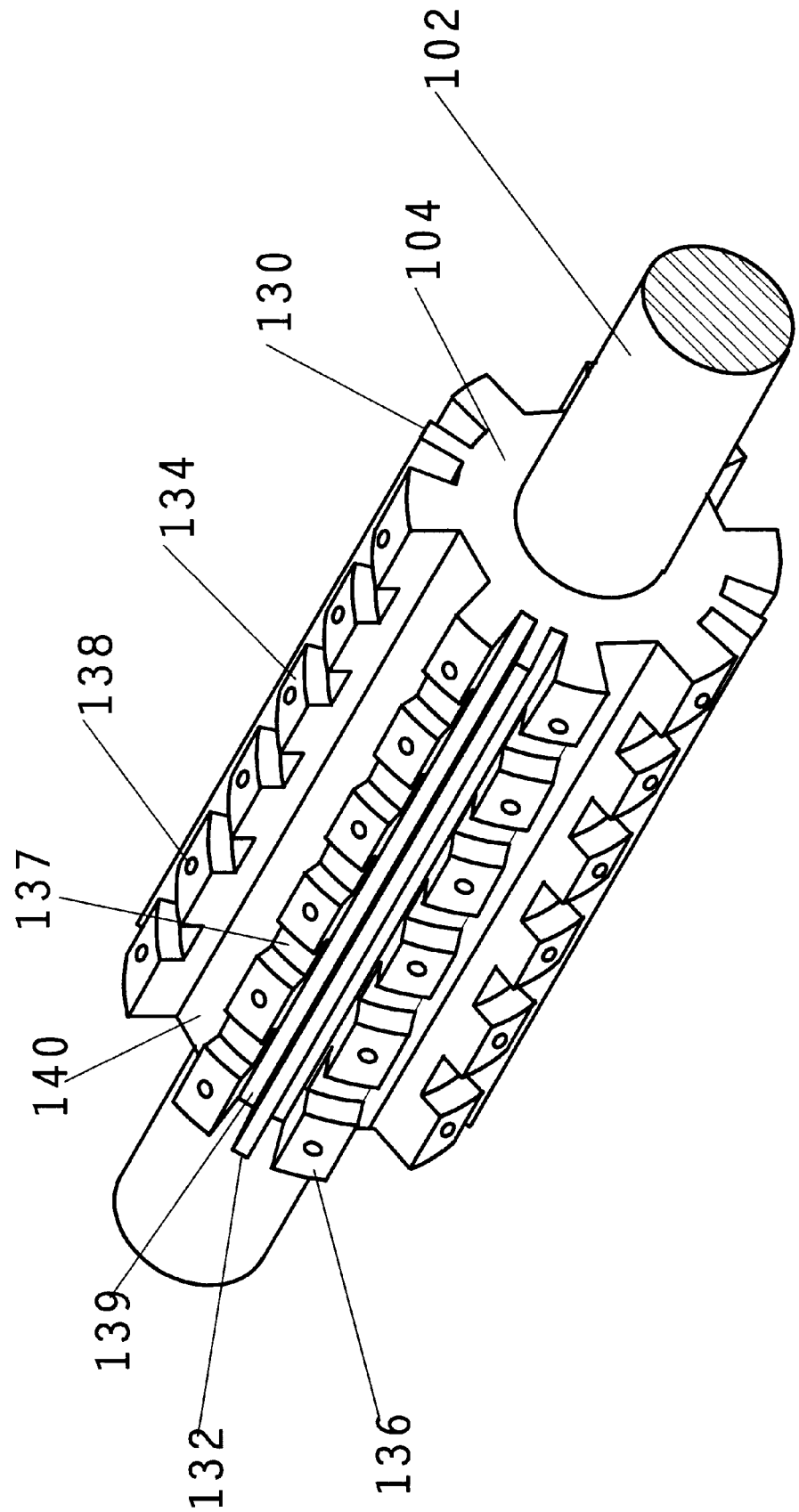
FIG. 2 is a perspective view of the shaft and body portions of the combination roller of FIG. 1.

FIG. 2 shows the shaft 102 and body 104 portions of the roller with the ultrasonic bonding anvil shoes and ultrasonic bonding anvil hold-down shoes removed. Additional features of the combination roller body may be seen including vanes or stand-offs 130, 132, 134, and 136 and holes 138 for receiving bolts or other fasteners. The body portion of the combination roller has an outer surface which defines an intermittent or interrupted surface defined by the extremities of the vanes or stand-offs 130, 132, 134, and 136. While this outer surface may conform to a cylindrical, hexagonal, octagonal or other similar shape, it is preferred that the outer surface of the body portion of the roller conform to a cylinder for ease of fabrication of the ultrasonic bonding anvil and ultrasonic bonding anvil hold-down shoes.

In a particularly preferred embodiment, the body portion of the combination roller is fabricated by machining grooves, slots, or channels in a cylinder. These grooves, slots, or channels are typified by narrow grooves or channels 139 and broader grooves or channels 140 in FIG. 2. The grooves, slots, or channels 139 and 140 extend inwardly from the surface of the body portion of the roller and extend for at least a portion of the length of the body portion of the combination roller. Certain of the vanes or stand-offs (for example 134 and 136) are also machined to form slots or channels 137 which permit air flow laterally between the longitudinal grooves, slots or channels 139 and 140.

The body 104 and shaft 102 portions of the combination roller may form a unitary assembly by machining a single piece, but advantages gained by forming the body and shaft portions of the roller as separate pieces make unitary fabrication less desirable. Preferred embodiments of the roller body are shown is FIGS. 3A and 3B. In FIG. 3A the body portion 104 of the combination roller is shown as a single piece with a hollow central core 153. The core 153 is shown as cylindrical in the embodiment depicted in FIGS. 3A and 3B, with key-ways 154 and 156. However, the hollow central core 153 can be of any surface shape which conforms to and fits closely with the outer surface of the shaft portion 102 of the combination roller. The one-piece body portion depicted in FIG. 3A is assembled to the shaft portion 102 of the combination roller by sliding the body portion 104 over the shaft portion 102 prior to assembling the resulting sub-assembly into the machine.

In FIG. 3B, the body portion 104 of the combination roller is shown, again as having a cylindrical hollow core 153 as in FIG. 3A, but with the body portion split into two pieces along longitudinal cuts 150 and 152. This embodiment has the advantage of permitting affixing the body portion pieces to the combination roller shaft portion after the latter has already been assembled to the machine. In both the one piece and split, two-piece, embodiments of the body portion 104 of the combination roller shown in FIGS. 3A and 3B, the body portions are affixed to the shaft portion 102 by bolts or other fasteners passing through holes 155 in the body portions 104. Both the one piece and split, two-piece, embodiments of the body portion 104 may be slideably moved along the shaft portion 102 of the roller prior to affixing the body portions 104 to the shaft portion 102. This permits variations in machine set-up to accommodate different product configurations.

Two alternative embodiments of the assembled body and shaft portions of the combination roller of the invention are shown in FIGS. 4A and 4B where element 202 represents a cut-away section of the machine frame and elements 206 and 208 represent cut-away bearing assemblies for the combination roller shafts 102. In FIG. 4A the body portion 104 of the combination roller is shown as a single longer section, and in FIG. 4B as two shorter separate sections 104A and 104B. It is to be understood that in both embodiments shown in FIGS. 4A and 4B that the body portions 104, 104A and 104B may be each of a single piece or in two or more split pieces as discussed above and depicted in FIGS. 3A and 3B.

Also shown in FIGS. 4A and 4B are end- or cap-plates 220, 222, 224, and 226 of combination roller body portions 104, 104A, and 104B. These end- or cap-plates are bolted or otherwise attached to the ends of the body portion 104, 104A and 104B of the combination roller and are provided with one or more apertures, each communicating with the grooves, slots, or channels 139 and 140 in the body portion mentioned above.

Figure 5:
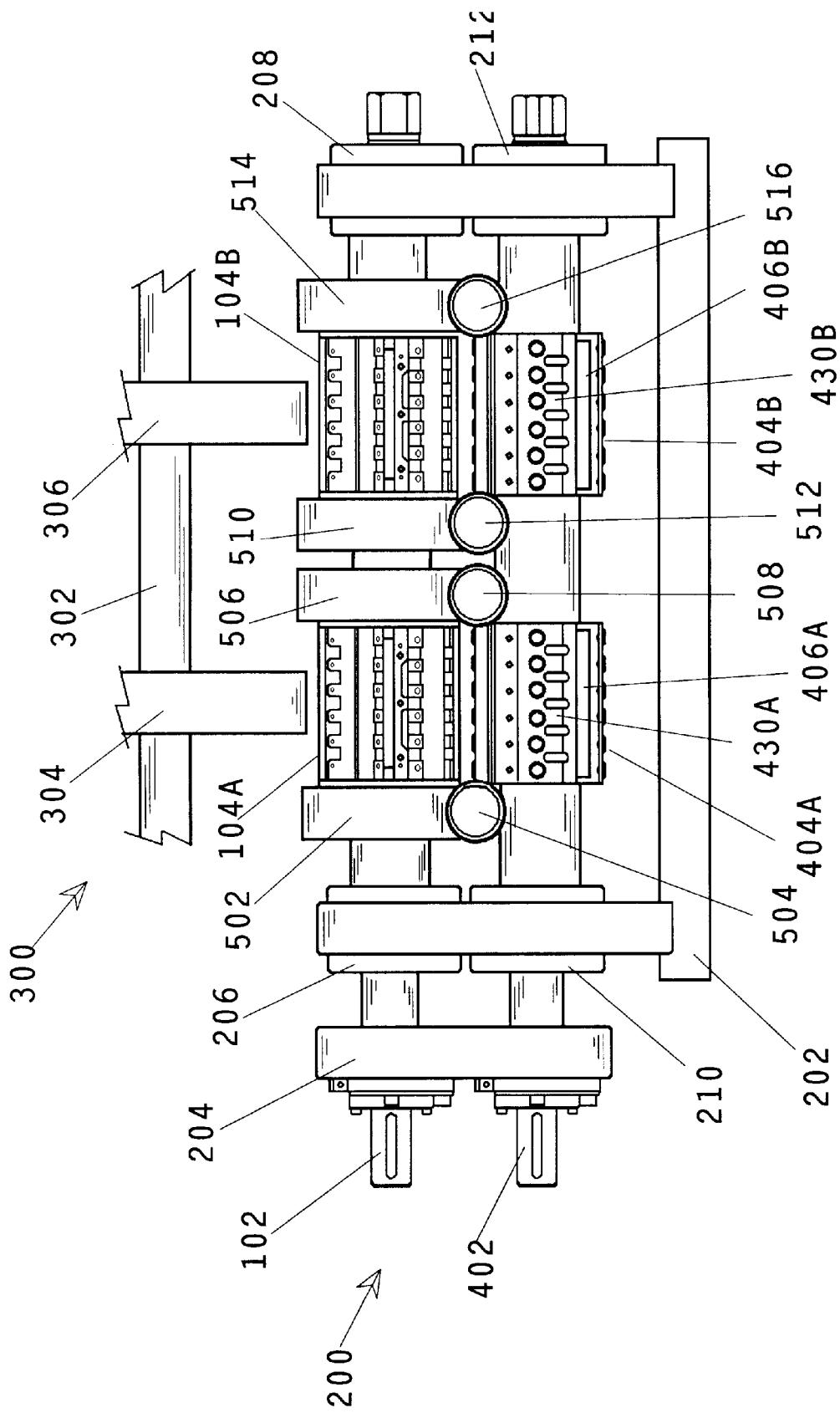
FIG. 5 is a front view of the combination roller and rotary cutter sub-assembly of the machine of the present invention.

FIG. 5 depicts the partially assembled roller sub-assembly of the machine of the invention incorporating the combination roller described above. In FIG. 5, the two-section roller body of FIG. 4B is shown assembled into machine frame 202 but without the ultrasonic bonding anvil shoes 112 and 120 or the ultrasonic bonding anvil hold-down shoes 110, 114, 118, and 122 of FIG. 1 attached. The sub-assembly also shows a two-section rotary cutter comprising rotary cutter shaft 402 and rotary cutter sections 404A and 404B. The shaft 102 of the combination roller and the shaft 402 of the rotary cutter are driven to contra-rotate by meshed 1:1 gears housed in gear-box 204.

Combination roller shaft 102 turns in machine frame 202 on bearing assemblies 206 and 208 and rotary cutter shaft 402 turns in machine frame 202 on bearing assemblies 210 and 212.

A rotary ultrasonic bonding horn apparatus 300 comprises two rotary ultrasonic bonding horns, of the type disclosed in U.S. Pat. Nos. 5,707,470 and 5,711,847. The contents of which are incorporated herein by reference. The rotary ultrasonic bonding horns are shown as partial elements 304 and 306 turning on shaft 302. The two horns are shown opposed to combination roller body portions 104A and 104B. In FIG. 5, the outside working surface of the rotary ultrasonic bonding horns 304 and 306 are shown somewhat spaced-apart respectively from combination roller sections 104A and 104B. This is because the ultrasonic bonding anvil shoes have been omitted from this Figure. As can be seen in the fully assembled roller sub-assembly of the machine depicted in FIG. 11, discussed further below, the outer surfaces of the installed ultrasonic bonding anvil shoes 120 and 112 are in close working relationship with the outer surfaces of the rotary ultrasonic bonding horns 304 and 306, respectively.

Vacuum commutators 502 and 506 are shown abutting, respectively, the end- or cap-plates 222 and 224 of roller body portion 104A and vacuum commutators 510 and 514 similarly abutting the end- or cap-plates 226 and 222 of roller body portion 104B. When the machine is operating, hoses (not shown) attached to vacuum take-off ports 504, 508, 512, and 516 draw air out of the vacuum commutators and, in a manner discussed further below, out of the channels of the combination roller body portions 104A and 104B.

Rotary cutter sections 404A and 404B are shown in FIG. 5 with respective cutter bars 406A and 406B and rotary cutter bar retainers 4308.

Rotary ultrasonic bonding horns 304 and 306 can be laterally and slideably positioned on shaft 302; vacuum commutators 502, 506, 510, and 514 and combination roller body portions 104A and 104B can be laterally and slideably positioned on combination roller shaft 102; and rotary cutter sections 404A and 404B can be laterally and slideably positions on rotary cutter shaft 402 to accommodate products of differing widths.

Figure 6:
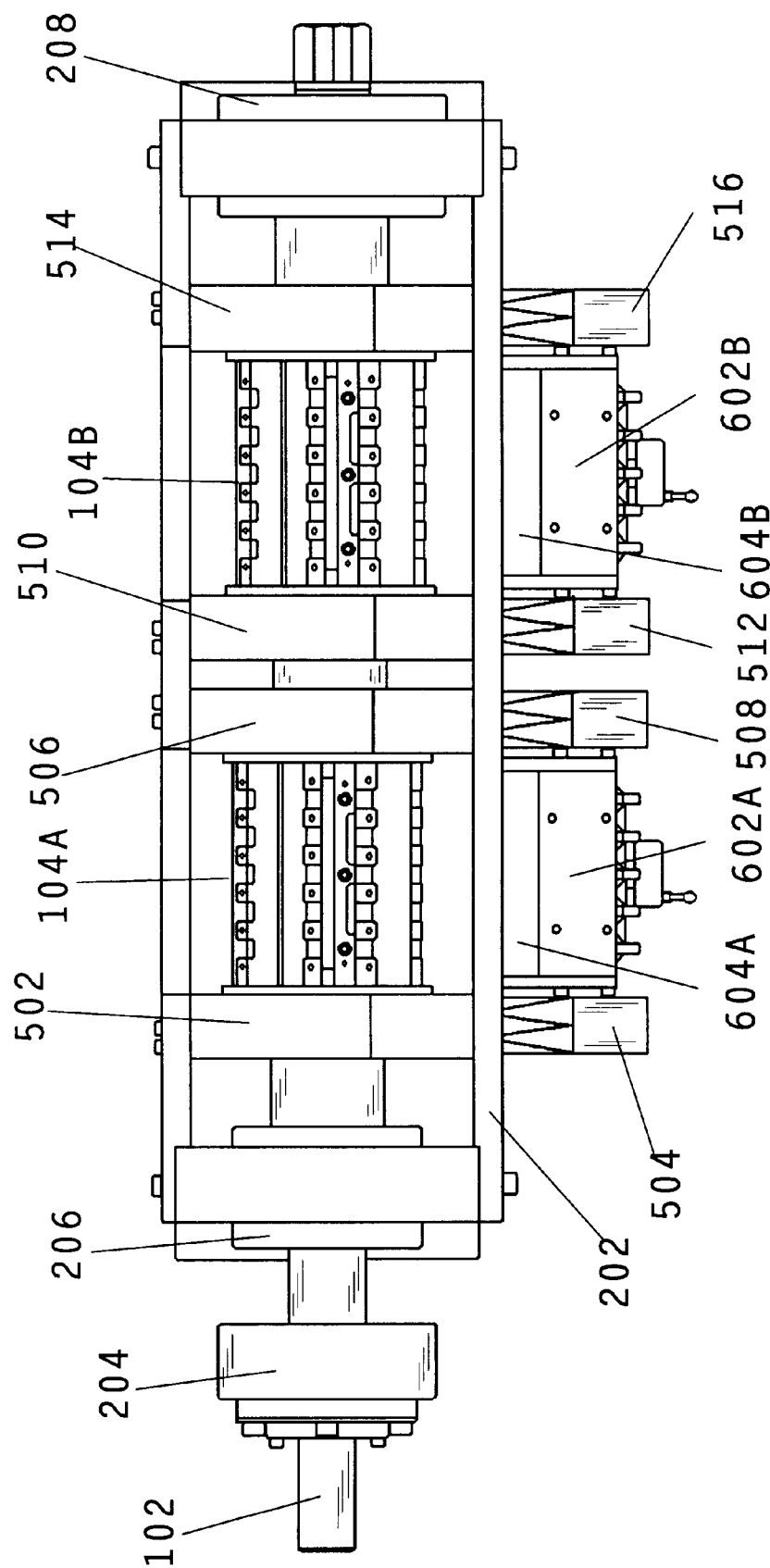
FIG. 6 is a top view of the machine sub-assembly of FIG. 5.

The roller sub-assembly of FIG. 5 is shown in top view in FIG. 6, with the rotary ultrasonic bonding horn assembly 300 of FIG. 5 removed. The top view shows the first and second rotary cutter blade oiler assemblies 602A and 602B with rotary cutter blade oiling rollers 604A and 604B. The oiling rollers are soft, typically sponge rubber, rollers which contact the cutting edge of the rotary cutter bar upon each rotation of the rotary cutter and deposit a light coating of oil on the cutter bar edge. Other elements of the roller sub-assembly shown in both the top view of FIG. 6 and the front view of FIG. 5 bear the same reference numerals.

Figure 7:
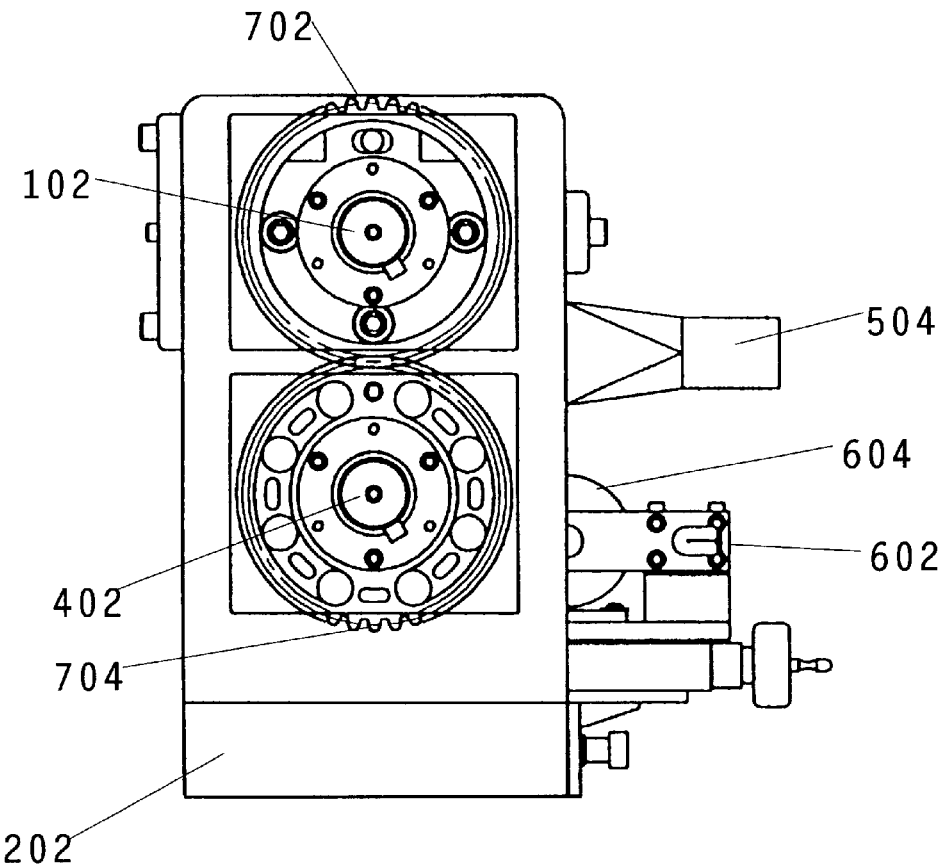
FIG. 7 is an end view of the machine sub-assembly of FIG. 5.
Figure 10:
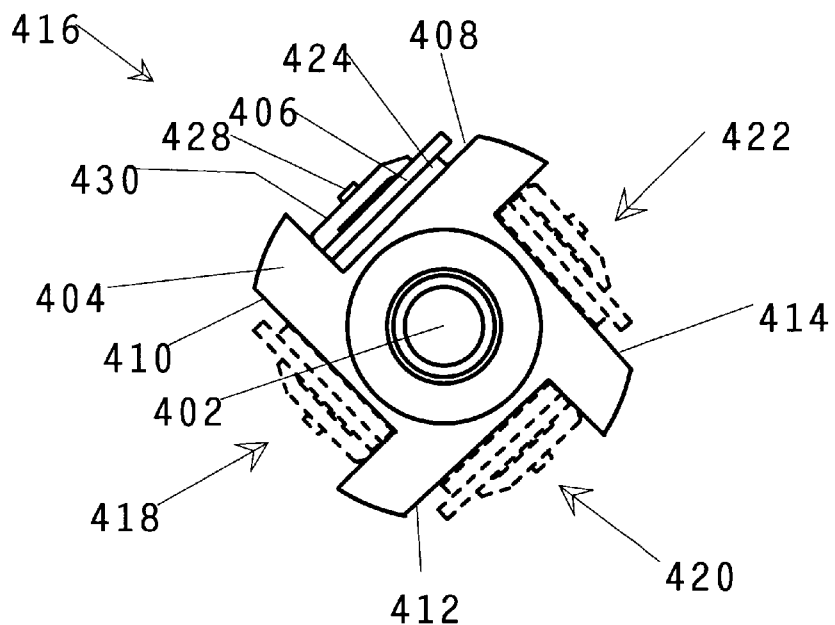
FIG. 10 is an end view of the rotary cutter of the machine sub-assembly depicted in FIGS. 5–7.

FIG. 7 shows the end view of the roller sub-assembly of FIGS. 5 and 6 with the gear-box cover 204 and the rotary ultrasonic horn assembly 300 of FIG. 5 removed. FIG. 7 shows the cutter blade oiler roller 604 as well as the meshed 1:1 gears 702 and 704 driving, respectively, the combination roller shaft 102 and rotary cutter shaft 104.

FIG. 8 shows in perspective view, vacuum commutator 502 of FIGS. 5 and 6. The commutator has a central opening 520 which accommodates the shaft portion 104 of the combination roller and a vacuum take-off tube 504. An arcuate groove 518 is machined into one face of the commutator 502 which arc subtends an angle i. The groove continues inside the commutator to communicate with the opening 522 in the vacuum take-off tube 504 as can be seen in the cross-sectional view of commutator 502 along cut line 9—9 depicted in FIG. 9. As shown in FIGS. 4 and 5, commutator 502 abuts end- or cap-plate 220. As the machine is operated, end- or cap-plate 220 rotates slideably against vacuum commutator 502. A aperture in end- or cap-plate 220 communicates with the slot 518 in commutator 502 during that portion of each rotation of the combination roller subtended by the arc i. During that portion of the rotation where the aperture in end- or cap-plate 220 is adjacent to the non-slotted face of vacuum commutator, the aperture is closed off and no air can be drawn from the commutator. The means by which this mechanism functions to hold cut workpieces to the outer working surface of the combination roller will be discussed further below.

Figure 11:
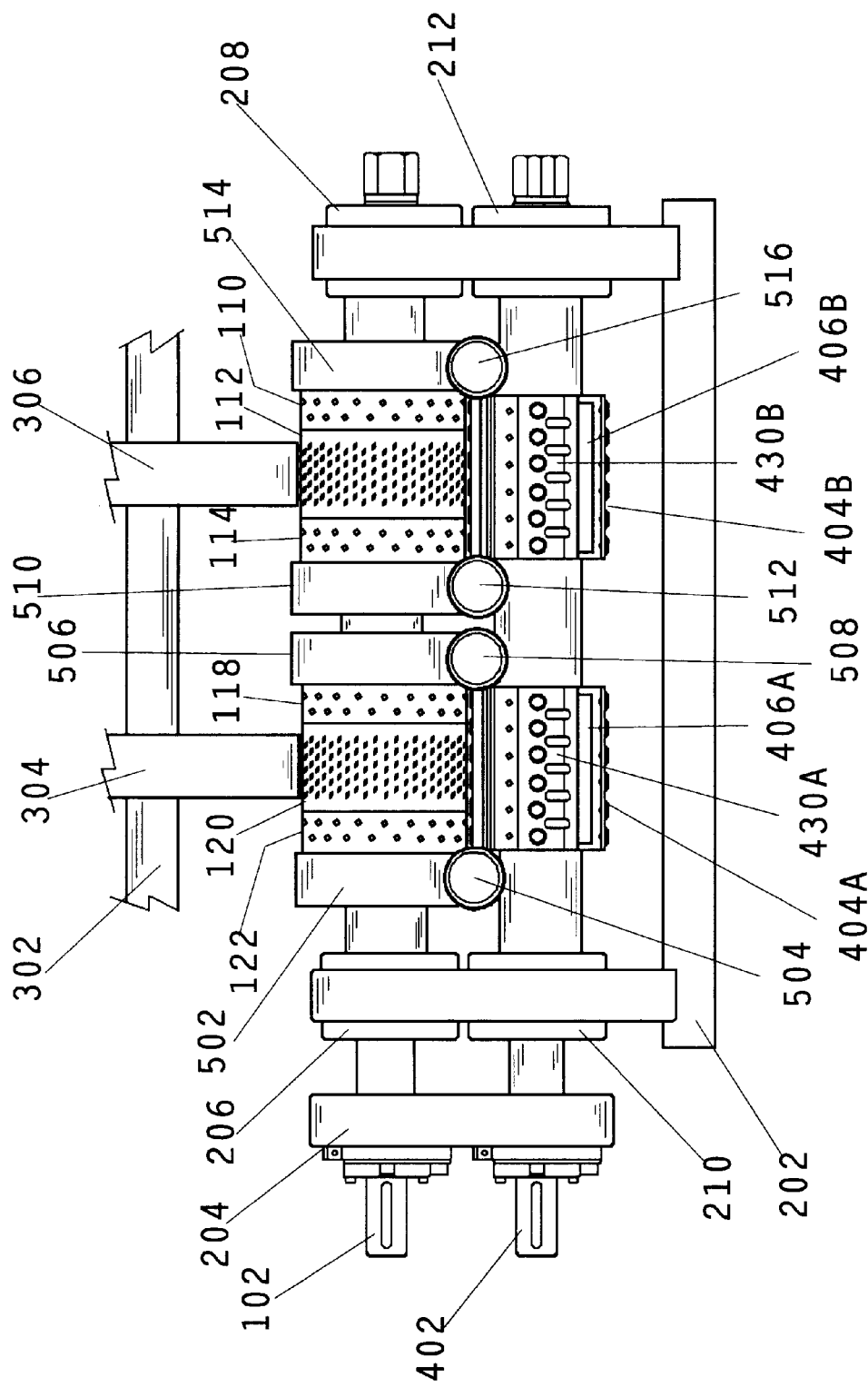
FIG. 11 is a front view of the machine sub-assembly shown in FIG. 5 with the ultrasonic bonding anvil shoes and ultrasonic bonding anvil hold-down shoes attached to the combination roller body.

The fully assembled roller sub-assembly of one embodiment of the machine of the invention is depicted in FIG. 11 which corresponds to the partial assembly of FIG. 5. The same elements in both Figures bear the same reference numerals. FIG. 11 shows the two sections of the body portion of the combination roller with the ultrasonic bonding anvil shoes 120 and 112 and ultrasonic bonding anvil hold-down shoes 122, 118, 114 and 112 fastened in place on the roller. It can be seen that, in the fully assembled roller sub-assembly of the machine, the outer working surfaces of the ultrasonic bonding anvil shoes 120 and 112 are in close working relationship with the outer working surfaces of the rotary ultrasonic bonding horns 304 and 306, respectively. As both the combination roller and the ultrasonic bonding horns contra-rotate with non-bonded materials passing between them, the vibratory action of the ultrasonic bonding horns working against ultrasonic bonding anvil shoes forms welds or bonds between the materials.

The ultrasonic bonding anvil shoes 120 and 112 and ultrasonic bonding anvil hold-down shoes 122, 118, 114 and 112 are depicted in greater detail in FIGS. 12–15. Both types of shoes comprise pieces having outer or working surfaces which are sections of a cylindrical surface. While the inside surfaces of both types of shoes are shown in the embodiments depicted in FIGS. 12–15 as also comprising sections of a cylindrical surface, the inner surface of the shoes can be of any shape or form which conforms to and fits closely with the outer surface of the combination roller body portion 104 described above. Thus, when the shoes are affixed to the body portion 104 of the combination roller, they form a cylindrical roller outer working surface.

Figure 12:
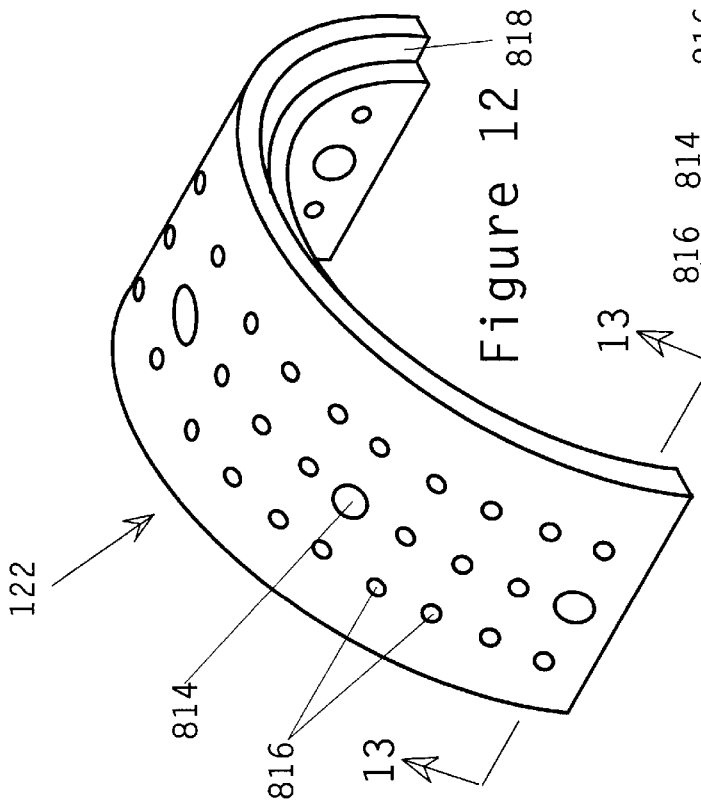
FIG. 12 is a perspective view of an ultrasonic bonding anvil hold-down shoe of of the combination roller of FIG. 1.

A typical ultrasonic bonding anvil hold-down shoe 122 is shown in FIG. 12 where vacuum apertures such as 816 are shown forming a pattern in the shoe. Bolt or fastener apertures 814 passing through the hold-down shoe receive bolts or fasteners for attaching the hold-down shoes to the vanes or stand-offs such as 132 and 134 of combination roller body portion 104 in fastener apertures or holes 138 on the vanes or stand-offs.

Figure 13:
FIG. 13 is a cross-sectional view of the ultrasonic bonding anvil hold-down shoe of FIG. 12, taken along cut line 13—13.

As can be seen in FIG. 12 and the cross-sectional view in FIG. 13, taken along cut line 13—13 of FIG. 12, one edge of the anvil hold-down shoes 122 are provided with a flange 818 which depends outwardly from the shoes in the direction of the width of the shoes. The flange 818 of the anvil hold-down shoes are inwardly facing flanges. The term "inwardly facing" flanges means that the outer or working surface of the anvil hold-down shoes are wider than the inner go surface of the shoes. While the embodiment depicted in FIGS. 12 and 13 shows an inwardly facing flange 818 on only one edge of the anvil hold-down shoe 122, the alternative embodiment where the hold-down shoe has inwardly facing flanges on both edges is also contemplated as falling with the scope of the invention.

Figure 14:
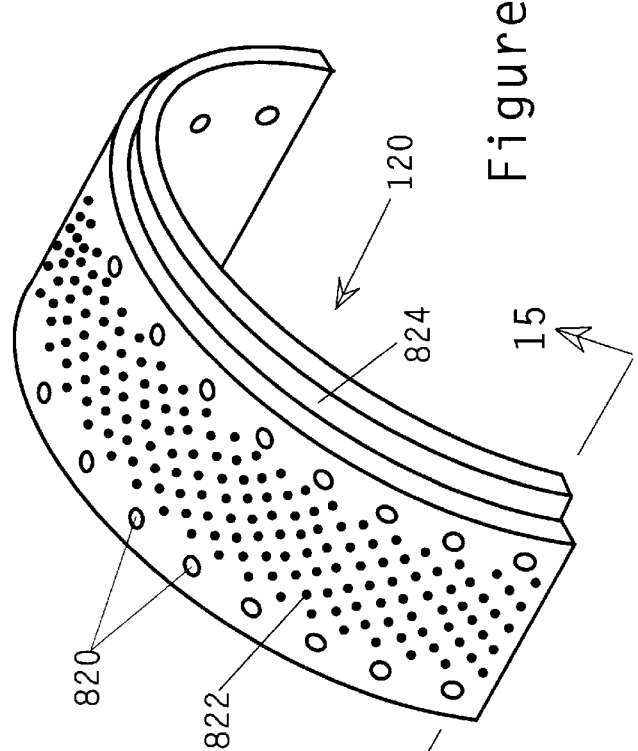
FIG. 14 is a perspective view of an ultrasonic bonding anvil shoe of the combination roller of FIG. 1.
Figure 15:
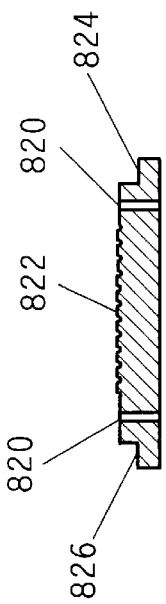
FIG. 15 is a cross-sectional view of the ultrasonic bonding anvil shoe of FIG. 14, taken along cut line 15—15.

The ultrasonic bonding anvil shoes are represented by ultrasonic bonding anvil shoe 120 depicted in FIG. 14 and the cross-sectional view of FIG. 15 taken along cut line 15—15 of FIG. 14. As with the hold-down shoes 122, the ultrasonic bonding anvil shoes 122 are provided with a pattern of vacuum apertures 820. In addition, the outer or working surfaces of the ultrasonic bonding anvil shoes are provided with a raised pattern of stippling, shown as a pattern of dots 822 in the embodiment depicted in FIGS. 14 and 15. The pattern may take any form, however, which effectively interacts with the working surface of the ultrasonic bonding horn to forms bonds between webs of materials passing between the two. The pattern of stippling is typically formed in the outer working surface of the ultrasonic bonding shoes by machining or chemically etching away a portion of the outer surface of the shoes to leave the stippling pattern. Initially the outside diameter of the prefabricated ultrasonic bonding anvil is a few mils (1 mil= 0.0254 mm) greater than the outside diameter of the hold-down shoes. The pattern of stippling which remains on the ultrasonic bonding anvil shoes after machining or etching is thus raised slightly above the surface of the anvil hold-down shoes.

Unlike the anvil hold-down shoes, however, the ultrasonic bonding anvil shoes are not provided with bolt or fastener holes or apertures. It has been found that when the ultrasonic bonding anvil shoes are, themselves, bolted or otherwise attached with fasteners to the combination roller body, the vibratory energy of the ultrasonic bonding horns tends to loosen or, in some instances, burn out the fasteners.

Instead, the edges of the ultrasonic bonding anvil shoes are provided with flanges 824 and 826 which depend outwardly from the anvils in the direction of the width of the anvils. The flanges 824 and 826 are outwardly facing by which is meant the inside surface of the ultrasonic bonding anvil shoe 120 is wider than the outside surface. The ultrasonic bonding anvil shoes are thus held firmly to the outer surface of the body portion 104 of the combination roller by flanking each ultrasonic bonding anvil shoe with a pair of hold-down shoes and bolting or other wise fastening the hold-down shoes to the combination roller body portion 104. The cooperative interaction of the inwardly facing flanges on the hold-down shoes and the outwardly facing flanges of the ultrasonic bonding anvil shoes urges the inside surface of latter against the outside surface of the combination roller body portion. In this manner, the ultrasonic bonding anvil shoes are held firmly in place on the roller body. Since the bolts or fasteners holding the anvil hold-down shoes are thus distanced from the rotary ultrasonic bonding horns, the problem alluded to above of vibratory loosening or burning off of the bolts or fasteners is considerably diminished.

When the anvil and anvil hold-down shoes are thus affixed to the combination roller body, vacuum tubular channels or cavities are formed between the inner surfaces of the shoes and the grooves, channels, or slots 139 and 140 in the combination roller body portion 104. These channels or cavities provide means for drawing air in through the vacuum apertures 816 and 820, respectively, in the anvil hold-down shoes 122 and the bonding anvil shoes 120. The tubes or channels permit the movement of air along the inside the assembled combination roller hub assembly. The slots or grooves 137 (cf. FIG. 2) permit lateral movement between adjacent channels or tubes in the assembled combination roller. In the manner described previously, holes or apertures in end- or cap-plates such as 220 communicate with these tubular channels and with slot 518 in the vacuum commutators 502 (cf. FIG. 8) abutting the end- or cap-plates 220.

Figure 16:
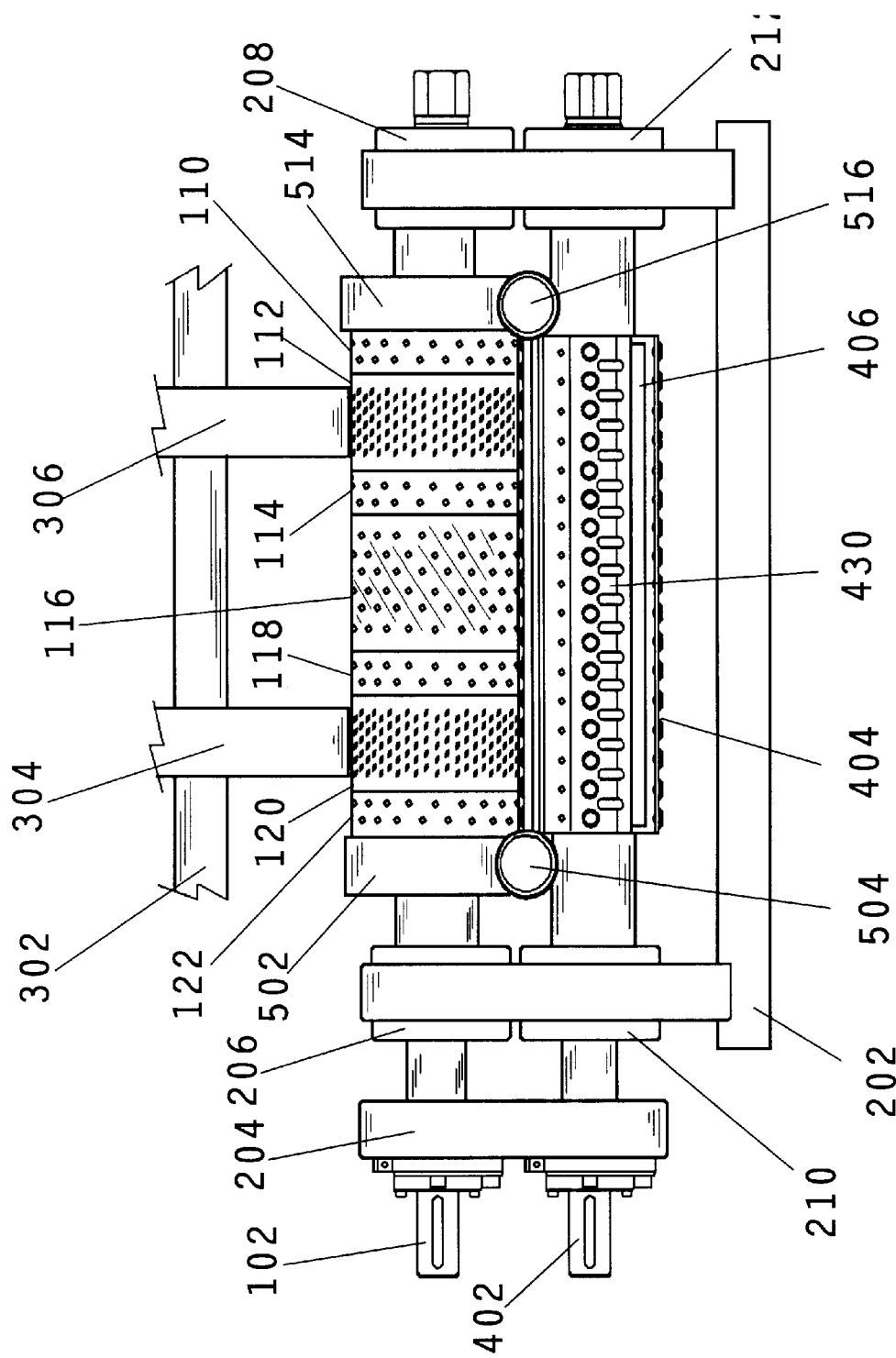
FIG. 16 is a front view of the machine sub-assembly employing the combination roller body and shaft shown in FIG. 4A with the ultrasonic bonding anvil shoes and ultrasonic bonding anvil hold-down shoes attached to the combination roller body.
Figure 17:
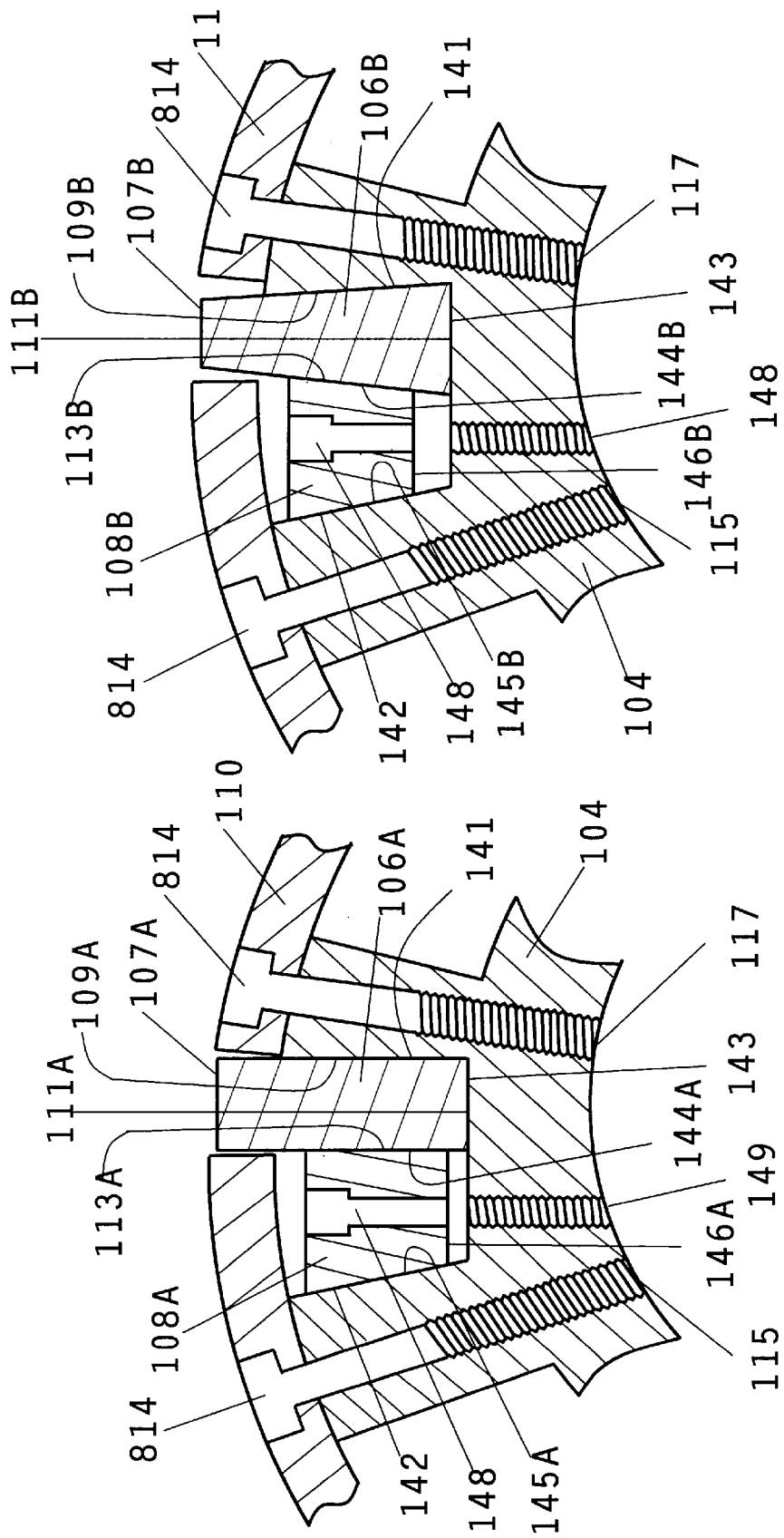
FIGS. 17A and 17B are partial sectional views of the combination roller body taken along cut line 2—2 of FIG. 1 showing alternative embodiments of the cutting anvil bar and cutting anvil bar retainer.

FIG. 16 shows an alternative embodiment of the fully assembled roller sub-assembly of the machine of the invention. In FIG. 16, all parts correspond to the same parts illustrated in FIG. 11, with the same parts in both Figures denoted by the same reference numerals. In FIG. 16, however, the underlying roller body is that of FIG. 4A. As a consequence, only two vacuum commutators 502 and 514 are required. The two sets of anvil shoes and anvil hold-down shoes, 122–120–118 and 114–112–110 in the embodiment shown, are separated by a spacer shoe 116. The spacer shoe 116, like the anvil hold-down shoes 122, 118, 114 and 112 are provided with vacuum apertures and bolt or fastener apertures. Since the spacer shoe is flanked by anvil hold-down shoes 118 and 114, it may or may not be provided with outwardly facing edge flanges, depending upon whether one or both edges of the flanking anvil hold-down shoes are provided with inwardly facing flanges.

This spacer shoe permits the passage through the machine of a wider substrate web. To accommodate webs of different widths, it is merely necessary to affix the spacer shoe of appropriate width on the combination roller body 104 and place the pairs of bonding anvil shoes and anvil hold-down shoes 122–120–118 and 114–112–110 on either side and attach them to the combination roller body.

One embodiment of a machine employing the combination roller described above is depicted schematically in FIG. 18. The machine 900 is shown in perspective view with uncut component webs 910 and 912 and substrate web 903 being fed through the machine. The webs 910 and 912 of uncut components are fed to the machine from supply rollers 909 and 911 and the substrate web 903 from supply roller 902 in the conventional manner.

Figure 18:
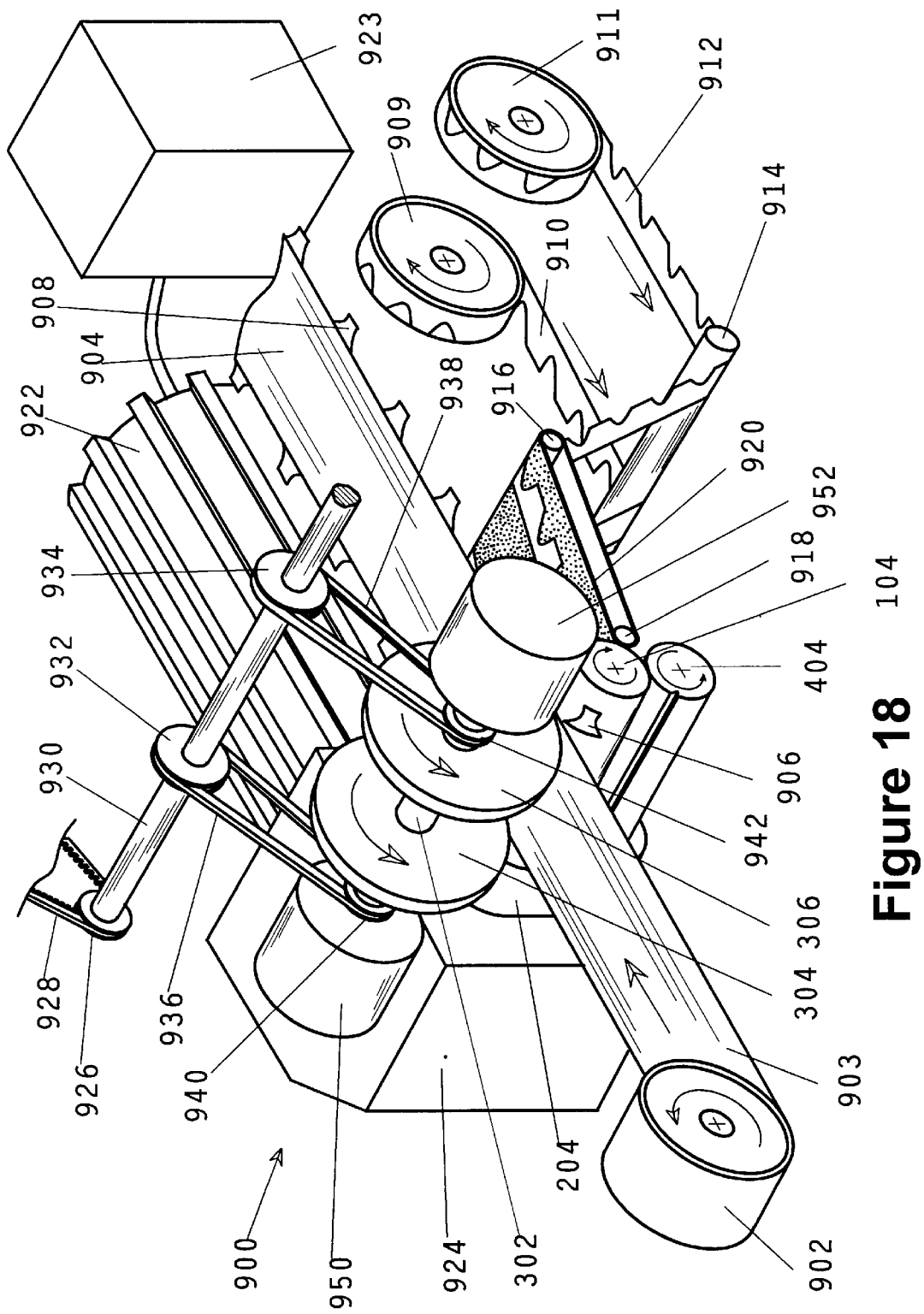
FIG. 18 is a schematic representation of one embodiment of the machine of the present invention with component and substrate webs shown passing through the machine.

The uncut component webs 910 and 912 are shown passing over a turning bar 914 and then over an endless belt conveyor 920 passing over rollers 916 and 918. In the manner described above, the uncut webs 910 and 912 of component material are received, and held by vacuum to, combination roller 104. As the webs 910 and 912 pass between combination roller 104 and rotary cutter 404, the webs are cut into discrete components which are held to the combination roller 104 by the vacuum means described above. In FIG. 18, one such cut discrete component 906 can be seen held to the outer working surface of combination roller 104.

As the rollers and webs move in the directions indicated by the arrows, the cut component 906 is moved into position on the underside of substrate web 903 where both the component 906 and the substrate web 903 pass between rotary ultrasonic bonding horn 306 and an ultrasonic bonding anvil shoe attached to, and forming a part of, the outer working surface of combination roller 104. The ultrasonic energy generated in the rotary horn 306 bonds component 906 to the substrate web 903. Simultaneously, a similar operation is occurring on the opposite edge of advancing web 903 with discrete components cut from web 910 by the cooperative action of rotary cutter 404, the combination roller 104 and rotary ultrasonic bonding horn 304. In FIG. 18, the finished substrate web, now indicated as 904, shown leaving the machine with bonded components 908 attached.

Rotary cutter 404 and combination roller 104 are driven by servomotor 922 which, in turn, is controlled by programmable controller 923. A right-angle gear-box 924 and meshed gears contained with gear-box 204 complete the transmission driving the contra-rotating rotary cutter 404 and combination roller 104. A separate motor (not shown) turns jack-shaft pulley 926 by means of gear-belt 928. The jack shaft 930, with attached pulleys 932 and 934 drive the rotary ultrasonic bonding horns 304 and 306 in the direction of the arrows by means of pulleys 940 and 942 on shaft 302 and gear-belts 936 and 938. The linear speed of the rotary ultrasonic bonding horns 304 and 306 is the same as the speed of the advancing substrate web 903.

Figure 19:
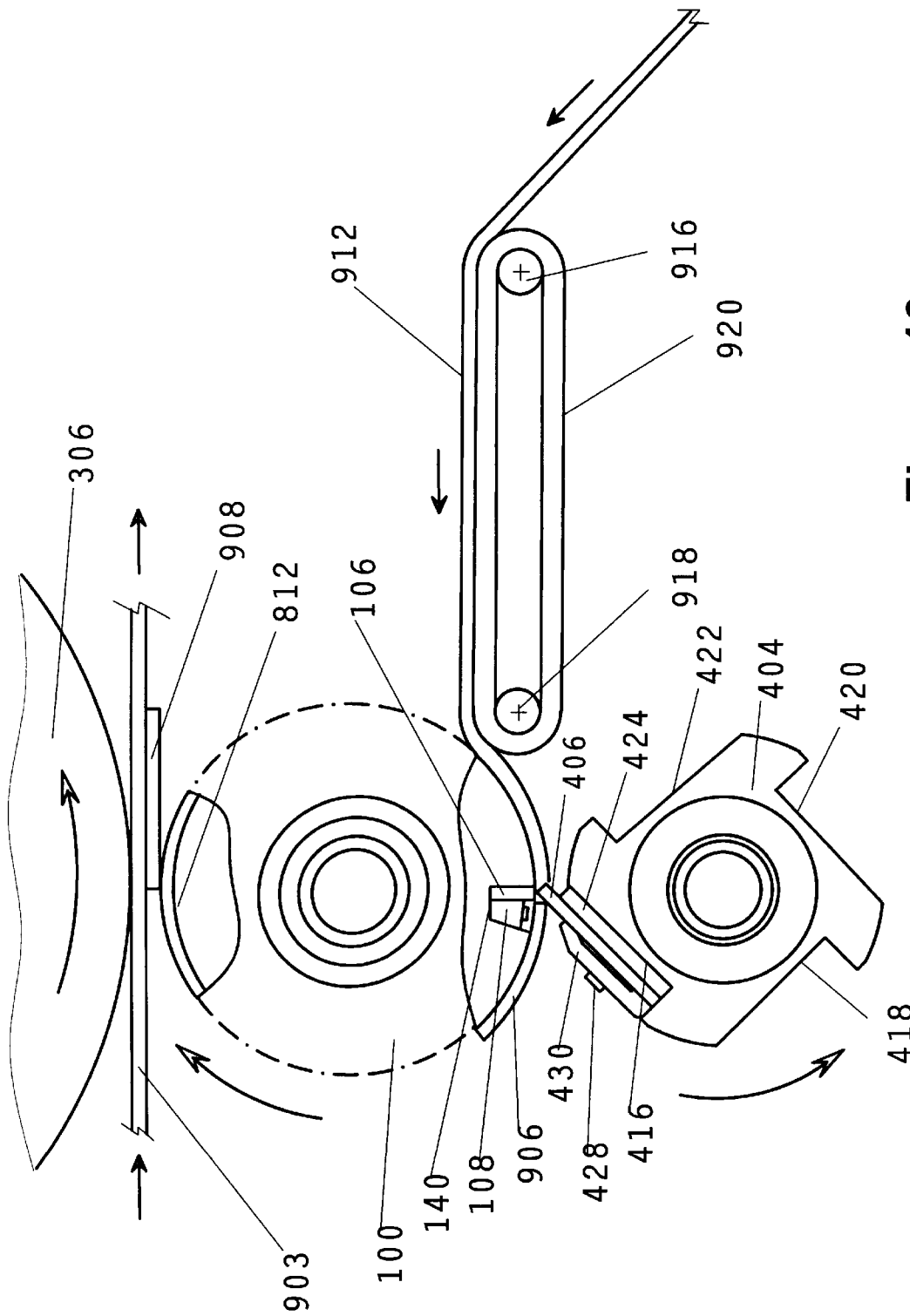
FIG. 19 is a schematic view of part of the machine of FIG. 18 showing the cooperating action of the rotary cutter and cutting anvil bar and the paths of the component and substrate webs through the machine.

The path of the webs through the machine, and the cooperative action of the rotary cutter and combination roller cutting anvil bar 106 is better seen in the detail view shown in FIG. 19. which is a partial end-view of the machine of FIG. 18. In FIG. 19. advancing uncut component web 912 passes over endless conveyor belt 920 and is picked up by the vacuum apparatus of combination roller 104. The component web 912, held to the outer working surface of combination roller 104 then passes through the nip between cutter bar 406 and combination roller cutting bar anvil 106 to cut the web into discrete workpieces 906. The cut workpiece 906, likewise held to the outer working surface of the combination roller 104, is moved into position on the underside of substrate web 903 where both the workpiece and the substrate web pass between combination roller 104 and rotary ultrasonic bonding horn 306. A workpiece component 908, prior in time in the process, is shown attached to substrate web 903, leaving the nip between the combination roller and ultrasonic bonding horn.

FIG. 19 shows in detail the function of the rotary cutter, illustrating features of the rotary cutter mentioned above. The rotary cutter body has been machined to have one or more flats; the embodiment shown in FIG. 19 shows four such flats, indicated as 416, 418, 420, and 422. The number of flats may vary from one to four, with one or three flats being preferred. More than four flats is theoretically possible on the rotary cutter, but such an arrangement becomes increasingly crowded.

In FIG. 19, one of these flats, 416, is shown occupied by a cutting bar apparatus which comprises a base plate 424, a cutting bar 406, a cutting bar retainer 430, and retainer bolt or fastener 428. As can be seen in FIG. 19, this arrangement permits the cutting bar 406 to strike the cutting anvil bar 106 on the combination roller 104 at an angle. This arrangement has two distinct advantages. First, the edge of the cutting bar 406 which strikes the cutting anvil bar 106 is only one of four such edges on the cutting bar. When this edge becomes dulled or nicked during operation of the machine, it is a simple matter of removing the bolts or fasteners 428 holding cutting bar retainer 430 and cutting bar 406 and turn the cutting bar to begin using a new edge. Second, the cutting bar 406 strikes the anvil bar at an angle and can thus flex, somewhat in the manner of a spring-board or diving board at a swimming pool. This eliminates the need for careful or precise placement of the cutting bar on the rotary cutter during machine set-up and operation.

Having described the parts and function of the illustrated embodiment of the machine, the method of selectively controlling and varying the speeds of the combination roller 104 and rotary cutter 404 will now be described.

As mentioned previously, the machine of the present invention employs a servomotor 922 for driving the shafts 102 and 402 of combination roller 104 and rotary cutter 404, respectively. Servomotors having the requisite torque are commercially available. A suitable servomotor for use in the machine of the present invention is available, for example, from the Indramat Division of Mannesmann Rexroth, 5150 Prairie Stone Parkway, Hoffman Estates, Ill. 60192. The servomotor is controlled by a Model DDS or HDS controller which has been programmed in the manner taught by the manufacturer using the desired speed profile for a given product.

Figure 20:
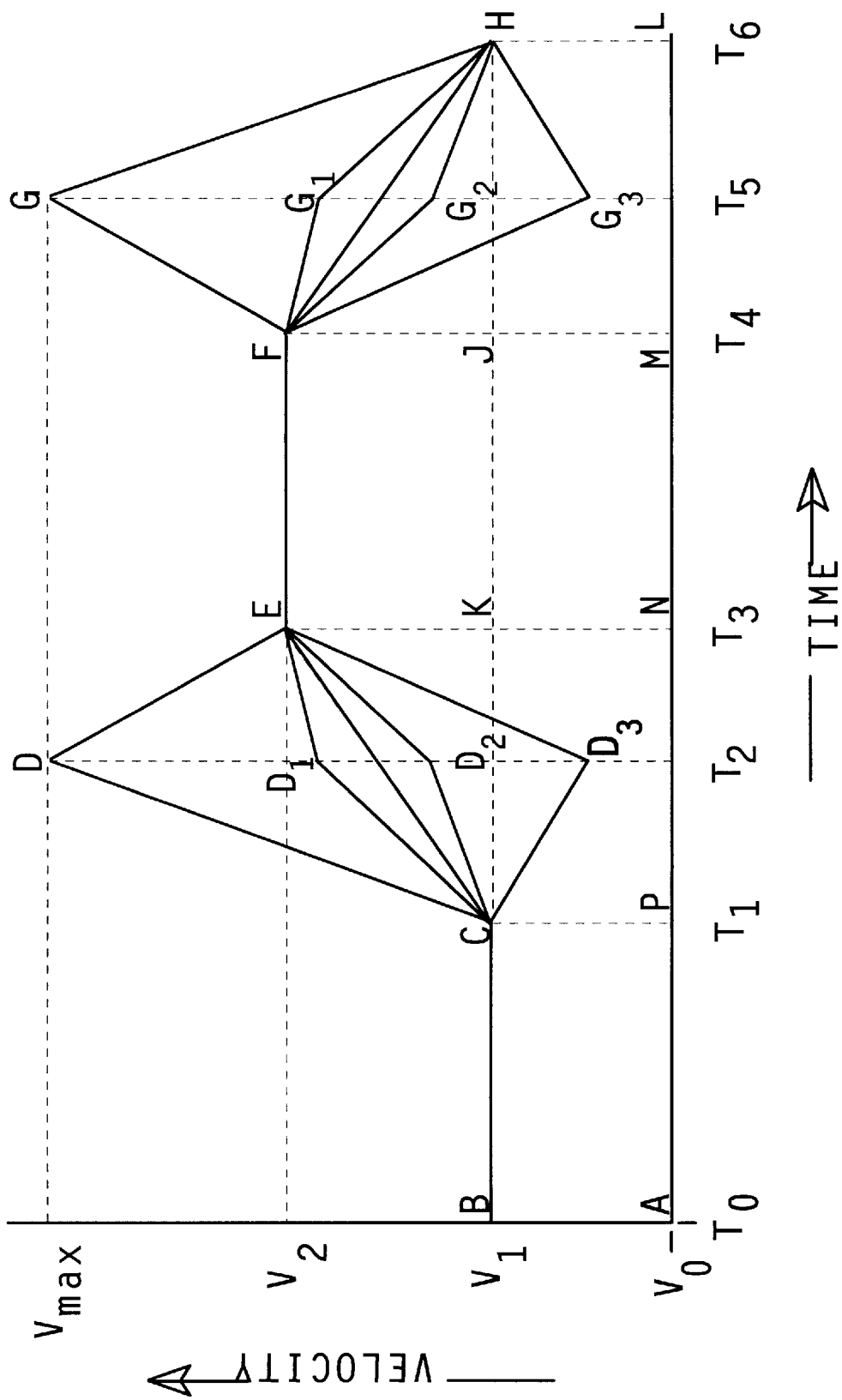
FIG. 20 is a representation of several speed profiles for the machine and process of the invention.

Speed profiles for one cycle of a process using the machine of the present invention are shown as solid lines in the graph depicted in FIG. 20. The vertical axis of the graph represents the linear speed at which the combination roller 104 and rotary cutter 404 are turning, and the horizontal axis represents time, with the interval between $T_0$ and $T_6$ representing the time required for one complete rotation of combination roller 104 and rotary cutter 404. Speed profiles for the combination roller and rotary cutter are represented by the solid lines which begin at point B, pass through points C, E, and F, and end at point H. Each speed profile comprises four distinct regions: (1) a first constant or dwell speed, $V_1$, represented by the horizontal line BC during time interval $T_0$ to $T_1$, (2) a period of speed change in the interval between $T_1$ and $T_3$, (3) a second constant or dwell speed, $V_2$, represented by the horizontal line EF in the time interval between $T_3$ and $T_4$, and (4) a period of speed change in the interval between $T_4$ and $T_6$, which returns the speed of the combination roller and rotary cutter to the original speed, $V_1$.

In the speed profiles represented in FIG. 20, the first speed, $V_1$, is shown as slower than the second speed, $V_2$. This corresponds to the situation depicted in FIG. 18 where workplace webs 910 and 912 are fed into the machine of the invention at a first slower speed because the components are closely spaced apart from one another on the workpiece web(s). In the speed profiles of FIG. 20, the second speed $V_2$ is faster than the first speed, $V_1$. This also corresponds to the situation of FIG. 18 where the substrate web 903 moves at a faster speed than the workpiece webs 910 and 912 to space the bonded components further apart on the substrate web than they were on the workpiece or component web(s). However, it will be apparent to one of ordinary skill in the art that the two speeds can be reversed in the machine and process of the invention; that is, $V_1$ can be faster than $V_2$. In such a situation, the workpiece components bonded to the substrate web will be spaced more closely together than on the supply workpiece web(s). In certain circumstances, this may lead to "shingling" or overlapping of the bonded workpiece components on the substrate web, and the machine and process of the invention can be used to produce such products, if desired.

Returning to the speed profiles of FIG. 20, the combination roller and rotary cutter speed change occurring in the intervals $T_1$ to $T_3$ and $T_4$ to $T_6$ can take on an unlimited number of shapes, a few of which have been illustrated in the Figure. The first speed change can follow, for example a profile represented by any of the solid lines CDE, $CD_1E$, CE, $CD_2E$, or $CD_3E$ or any similar variant. Likewise, the combination roller and rotary cutter speed change in the interval between $T_4$ and $T_6$ can follow a profile represented by the lines FGH, $FG_1H$, FH, $FG_2H$, or $FG_3H$ or any similar variant, in a manner independent of the first speed change profile.

It should be noted that, while the exemplified speed profiles in the speed change intervals $T_1$–$T_3$ and $T_4$–$T_6$ are shown as rectilinear, the profiles shown in FIG. 20 can also be curvilinear. That is to say, speed change profile CDE, shown as a line of acceleration CD and a line of deceleration DE, could be represented by a line breaking at two, three, or more intermediate points. Following this to its logical extreme, the line CDE would be a smooth curve between points C and E having a maximum at point D. It is preferred, however, that the speed profile in the speed change intervals $T_1$–$T_3$ and $T_4$–$T_6$ each be defined by a single "break point" to simplify determination of the overall speed profile, although, it has been found that the majority of cases of cutting and bonding can be accommodated by the straight line acceleration CE and deceleration FH.

It has been found that when the operating speed profile of the machine of the invention is measured, programming an idealized rectilinear speed profile such as BCDEFGH into the controller for the servomotor results in an actual observed speed profile in which regions CDE and FGH are curvilinear, while closely following profile the straight lines CDE and FGH. This will be readily understood by one of ordinary skill in the machine arts, who realizes the difficulty of abrupt changes in motor and roller speed such as would be required at points D and G in the idealized speed profile. Thus both rectilinear and curvilinear speed profiles for the speed change intervals $T_1$–$T_3$ and $T_4$–$T_6$ are contemplated as falling within the scope of the invention.

It is fundamental to the development of the velocity profile that the area under the line BCDEFGH (i.e. the integral of the speed profile function with respect to time) be set equal to the length of the circumference of the combination roller. With this fundamental "rule" set, it is possible to develop profiles which utilize the machine to manufacture articles having an almost infinite number of component configurations without requiring elaborate retooling of the machine.

That is, as the spacing of the uncut components on the component supply web and the required spacing of the components bonded to the substrate web differ from one product to another, the roller speeds $V_1$ and $V_2$ must be changed, relative to one another. Such a change results in a corresponding change in the area under the speed profile, which would ordinarily require an attendant change in the roller circumference (i.e. a grade machine change). However, in the machine and process of the present invention, as product line changes require changes in the roller speeds $V_1$ and $V_2$, the total AREA under the speed profile (i.e. the machine roller circumference) is kept constant by the simple expedient of appropriate adjustment in the speed profile in the speed change intervals $T_1$–$T_3$ and $T_4$–$T_6$. The only limitation on this being the ability to complete an acceleration or deceleration within the allotted time based upon the torque available from the motor driving the roller. The required torque is the slope of the acceleration or deceleration multiplied by the roller inertia. Also, knowing that the time interval $T_0$–$T_6$ represents the time for one complete product cycle, and given the available servo motor torque, the maximum machine speed (product/second) can be readily calculated.

As stated earlier, the dwell speeds $V_1$ and $V_2$ are determined by the spacing of the components on the supply workpiece web and their desired spacing when bonded to the substrate web for a particular product line. The profile AREA is defined by ¼, ½, ¾, or 1 rotation of the combination roller, and the time interval $T_0$–$T_6$ corresponds to the product cycle for each AREA. The profile AREAs are changed to 1, 2, 3, or 4 times per roll revolution to better fit product specifications and match acceleration to available torque and desired machine speed. Therefore, all of the values of $V_1$, $V_2$, $T_1$, $T_3$, $T_4$, $T_6$, and the area under speed profile are thus established by requirements of the product configuration or machine roller diameters. All that remains in determining a speed profile is the determination of the "break points" in the speed change intervals.

Referring to FIG. 20, an "ideal" speed profile is represented by the solid line BCEFH. This "ideal" speed profile represents one in which the machine is "tailor-made" to the particular product line, that is, a machine in which the roller circumference is chosen to be equal to the area bounded by a speed profile having two constant dwell speeds equal to the web speeds, and periods of smooth, linear acceleration and deceleration. The line BC represents the slow dwell speed at which the component web is received and cut into components. The solid line CE represents an interval of simple linear acceleration to the faster substrate web speed during which interval the speed of the combination roller and cut workpiece process are changed to meet the faster speed of the advancing substrate web. The line EF represents the faster dwell speed during the interval where the cut workpiece is bonded to the substrate web. Finally, solid line FH represents the interval during which the combination roller speed is changed to again match the slow speed of the workpiece or component web, thus completing one cycle of the machine operation.

In this "ideal" situation, the roller circumference would be fixed by the length corresponding to the irregular area bounded by the lines joining the points ABCEFHL. If one were to use the machine to make a different product where the product configuration required moving, for example, speed $V_2$ to a lower value while leaving $V_1$ at its former value, the result would be a decrease in the area bounded by lines joining points ABCEFHL. If the speed profile were to remain an "ideal" profile, the area under the profile would correspondingly decrease, requiring a decrease in the machine roller circumference. The machine of the present invention permits a simple "electronic grade change" when moving to the new product line rather than requiring such a complicated machine change. The total area under the speed profile in the machine and process of the invention is kept constant by simply adding area to or subtracting area from the area under the "ideal" speed profile as $V_2$ is moved with respect to $V_1$.

It is readily apparent to one of ordinary skill in the machine arts that matching $V_1$ to the in-feed product for the ideal time span $T_0$–$T_1$ is a physical impossibility for a single variable velocity roll as described here. In the situation where a workpiece component patch of length X is placed on a product of length Y, it is understood that component patch X is fed at a rate of one X per one product Y. Since the component patch having length X is fed once per product of length Y, and the perfect time interval is $T_0$–$T_6$, it is only possible to match the in-feed speed ($V_1$) for a fraction of the in-feed time, and therefore $T_0$–$T_1$ must be less than $T_0$–$T_6$. It has been found through experimentation with the machine of the present invention that matching $V_1$ is generally only critical during the instant of cutting and that the roller speed can be mis-matched from the patch speed during the pre-cut in-feed interval. The machine of this invention does, however, match the $V_2$ bonding speed since the $V_2$ time interval $T_3$–$T_4$ is naturally a fraction of the product time cycle $T_0$–$T_6$.

It is to be understood that in FIG. 20 and in the discussion which follows, the speed $V_2$, and its graphical representation, line EF, is upwardly or downwardly moveable, carrying with it points E and F and the lines attached thereto. The various speed profiles shown in FIG. 20 have been shown with a common line EF to avoid unnecessarily cluttering the figure.

In the hypothetical case of speed profile BCDEFGH, the substrate web speed, $V_2$ has been lowered with respect to workpiece web speed $V_1$. To maintain the area under the speed profile constant (to match the fixed machine combination roller circumference), "excess" triangular areas bounded by lines joining the points CDE and points FGH are added. This area is generated by over-accelerating the roller to a speed greater than $V_2$, and decelerating back down to $V_2$ in the first speed as change interval, and over-accelerating the roller to a speed greater than $V_2$, and decelerating back down to $V_1$ in the second speed change interval.

In another hypothetical example, were the product configuration to require raising $V_2$ with respect to $V_1$, it would be necessary to subtract area from the area under the speed profile. Such a situation is represented, for example by speed profile $BCD_2EFG_2H$. In that case, the triangular areas $CED_2$ and $FHG_2$ would be subtracted from the "ideal" profile area to maintain the area constant. In this manner, the mechanical features of the machine (roller diameter and circumference) may remain unchanged while the servomotor driving the roller is re-programmed electronically to accommodate product line changes.

Figure 21:
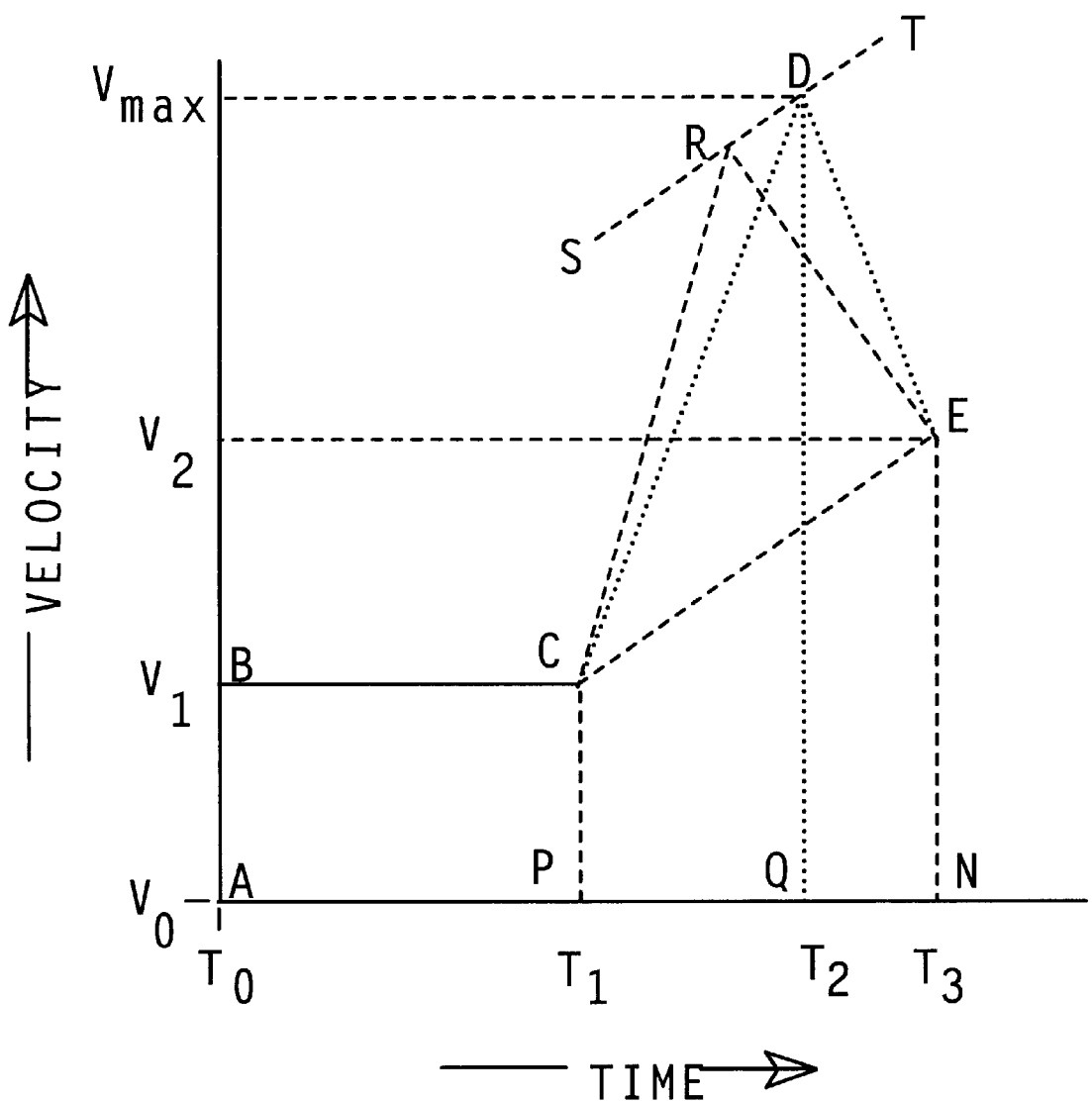
FIG. 21 is a representation of one method of determining a speed profile for the machine and process of the invention.

The values of maximum velocity D and G, corresponding to coordinates $V_{max}$, $T_2$ and $T_3$ are determined as illustrated in FIG. 21 where the initial portion of speed profile BCDEFGH is illustrated. The total area under that speed profile is the irregular area bounded by the lines jointing points ABCDEFGHL of FIG. 20. If the preferred choice is made to divide the excess speed area into equal triangular areas CDE and FGH, the area under the triangle CDE, $Area_{CDE}$, is equal to:

$$Area_{CDE}=(Roller\ circumference)/2-Area_{CEK}-Area_{EFJK}-(Area_{ABHL})/2$$

Correspondingly, the area under the triangle FGH, $Area_{FGH}$, is equal to:

$$Area_{FGH}=(Roller\ circumference)/2-Area_{FHJ}-(Area_{ABHL})/2.$$

Once the area of triangle CDE is known, point D is determined as illustrated in FIG. 20. Referring to FIG. 21, a right triangle CER is constructed on the base line CE which runs between coordinates $T_1$, $V_1$ and $T_3V_2$ by dropping a line perpendicular to line CE passing through the coordinate $T_3V_2$ (point E) and extending it to point R such that its length, $Length_{WER}$, is equal to:

$$Length_{ER}=sqrt[(T_3-T_1)^2(V_2-V_1)^2]$$

Next, a line ST of slope equal to the slope (acceleration) of line CE is then constructed to pass through point R. The point D falling on line ST is then determined such that the angles CDQ and QDE are equal. This point defines the dotted lines CD and DE and fixes point D which, in turn determines $V_{max}$ and $T_2$. In a similar manner, the value of $T_5$ is also determined.

Once the velocity values of $V_1$, $V_2$, $V_{max}$, and the time values $T_1$, $T_2$, $T_3$, $T_4$, $T_5$ and $T_6$ are determined for a particular product, a data table of velocity for n points along the time axis of the speed profile is generated. The resulting data table is used as the data control set for controlling the variable speed of the servomotor during each revolution of the machine rollers. For example, a data table of roller speed at each 1/2000 revolution is constructed. These data are fed into the servomotor controller drive the servomotor, combination roller, and rotary cutter to operate at the desired speeds. To convert the machine to the production of a new product with different configuration, it is merely necessary to generate a new data table for that product to drive the servomotor.

While there has been shown and described the preferred embodiments of the machine and process of the present invention, it will be clear to one of skill in the art that various modifications in the machine and process can be made without departing from the scope of the invention as it is described in the appended claims.

We claim:

1. A process for cutting discrete workpieces from a first uncut workpiece web moving at a first workpiece web speed and transferring and bonding said cut discrete workpieces to a substrate web moving at a second substrate web speed comprising carrying out on a single roller the steps of:
    a) receiving on said roller said first uncut workpiece web and cutting discrete workpieces from said first uncut web on said roller while said roller is moving during a first fraction of its rotation at or near said first workpiece web speed and holding said cut discrete workpieces to said roller by vacuum means;
    b) changing the speed of said roller and said discrete workpieces to match the speed of said second substrate web during a second fraction of rotation of said roller;
    c) transferring said discrete workpieces to said second substrate web and bonding said discrete workpieces to said substrate web while said roller is moving for a third fraction of its rotation at said second substrate web speed; and
    d) changing the speed of said roller to approach the speed of said first workpiece web during a fourth fraction of rotation of said roller.

2. A process according to claim 1 wherein said first, second, third, and fourth fractions of rotation of said roller comprise equal fractions of one rotation of said roller.

3. A process according to claim 1 wherein one of said step b) and step d) of changing the speed of said roller comprises non-linear acceleration.

4. A process according to claim 3 wherein said non-linear acceleration comprises at least two periods of unequal linear acceleration.

5. A process according to claim 3 wherein said non-linear acceleration comprises continuous curvilinear acceleration.

6. A process according to claim 1 wherein said first workpiece web speed is slower than said second substrate web speed.

7. A process according to claim 1 wherein said first workpiece web speed is faster than said second substrate web speed.

8. A process according to claim 5 wherein one of said first and said second accelerations is non-linear.

9. A process according to claim 6 wherein one of said first and said second accelerations is non-linear.

10. A process according to claim 7 wherein said non-linear acceleration comprises at least two periods of unequal linear acceleration.

11. A process according to claim 8 wherein said non-linear acceleration comprises continuous curvilinear acceleration.

12. A process according to claim 9 wherein said non-linear acceleration passes through a speed greater than said second substrate web.

13. A process according to claim 10 wherein said non-non-linear acceleration passes through a speed greater than said second substrate web.

14. A process according to claim 9 wherein said non-linear acceleration passes through a speed slower than said first component web.

15. A process according to claim 10 wherein said on-linear acceleration achieves a speed slower than said first workpiece web.

16. A process for cutting discrete workpieces from a first uncut workpiece web moving at a first slower workpiece web speed and transferring and bonding said cut discrete workpieces to a substrate web moving at a second faster substrate web speed comprising carrying out on a single roller the steps of:

a) receiving on said roller said first uncut workpiece web and cutting discrete workpieces from said first uncut web on said roller while said roller is moving during a first fraction of each rotation at or near said first slower workpiece web speed and holding said cut discrete workpieces to said roller by vacuum means;

b) changing the speed of said roller and said discrete workpieces to a first temporary speed different from that of said first workpiece web speed and said second substrate web during a second fraction of each rotation of said roller and then changing the speed of said roller and discrete workpieces to match the speed of said second substrate web during a third fraction of each rotation of said roller;

c) transferring said discrete workpieces to said second substrate web and bonding said discrete workpieces to said substrate web while said roller is moving for a fourth fraction of each rotation at said second substrate web speed; and d) changing the speed of said roller to a second temporary speed different than that of said first workpiece web and said second substrate web during a fifth fraction of each rotation of said roller and then changing the speed of said roller and discrete workpieces to match the speed of said second substrate web during a sixth fraction of each rotation of said roller.

17. A process according to claim 16 wherein said first and second temporary speeds of said roller are greater than that of said second substrate web speed.

18. A process according to claim 16 wherein said first and second temporary speeds of said roller are intermediate between said first component web speed and said second substrate web speed.

19. A process according to claim 16 wherein said first and second temporary speeds of said roller are less than said first component web speed.

20. A combination roller having a length and an outer working surface, a central shaft portion having a length and an outer surface, and a body portion having a length and an outer surface, said combination roller having integral a) cutting anvil apparatus for engaging the cutting edge of a rotary cutter disposed in cooperative working relationship with said combination roller;

b) vacuum transfer apparatus for receiving and holding a first uncut web of workpieces to the working surface of said combination roller and for cutting said first web into discrete workpieces between said cutting edge of said cooperative rotary cutter and said cutting bar anvil and for holding said discrete workpieces to said working surface and transferring said discrete workpieces to a second substrate web; and c) ultrasonic bonding anvil apparatus for cooperating with the outer working surface of a rotary ultrasonic horn to thereby create bonds bonding the cut discrete workpieces to the second substrate web.

21. A combination roller according to claim 20 wherein the outer surface of said body portion defines an intermittent surface, said body portion having grooves which extend over a portion of the length of said body portion, said grooves depending inwardly from said intermittent surface of the body portion toward said central shaft, each of said grooves defining first and second side walls and a bottom wall.

22. A combination roller according to claim 21 wherein said body portion and said shaft portion of said combination roller are of one piece.

23. A combination roller according to claim 21 wherein said body portion and said shaft portion are separate and discrete pieces.

24. A combination roller according to claim 23 wherein said separate body portion has an inner surface, the inner surface of said separate body portion conforming to and fitting closely with the outer surface of said separate shaft portion.

25. A combination roller according to claim 24 wherein said body portion is moveably positionable along the length of said shaft portion.

26. A combination roller according to claim 23 wherein said body portion is split into two or more pieces longitudinally along the length of said body portion.

27. A combination roller according to claim 23 wherein said body portion comprises two or more sections spaced apart along the length of said combination roller shaft.

28. A combination roller according to claim 21 wherein the first sidewall and the bottom wall of at least one of said grooves form a first dihedral angle of 90° or less with one another, and the second side wall and bottom wall of said at least one grooves form a second dihedral angle of greater than 90° with one another.

29. A combination roller according to claim 26 wherein said cutting anvil apparatus comprises a cutting anvil bar and cutting anvil bar retainer; each of said cutting anvil and said cutting anvil retainer having top and bottom walls, first and second side walls and first and second end walls.

30. A combination roller according to claim 29 wherein said first side wall and said bottom wall of said cutting anvil form a dihedral angle with one another equal to said first dihedral angle of said at least one groove and said second side wall and said bottom wall of said cutting anvil bar retainer form a dihedral angle equal to said second dihedral angle of said at least one groove; whereby said cutting anvil bar and said cutting anvil bar retainer are received into said at least one groove of said combination roller, with the first side wall and bottom wall of said cutting anvil abutting respectively the first side wall and bottom wall of said at least one groove and said second side wall of said cutting anvil bar retainer abutting the second side wall of said at least one groove with the first side wall of said cutting anvil bar retainer abutting the second side wall of said cutting anvil to urge said first side wall of said cutting anvil bar against the first side wall of said at least one groove thereby retaining said cutting anvil bar in said at least one slot.

31. A combination roller according to claim 29 wherein said cutting anvil bar extends for at least a portion of the length of said combination roller.

32. A combination roller according to claim 29 wherein said cutting anvil comprises a bar having a rectangular cross-section.

33. A combination roller according to claim 29 wherein said cutting anvil comprises a bar having a trapezoidal cross-section.

34. A combination roller according to claim 33 wherein the top and bottom surfaces of said cutting anvil bar are parallel.

35. A combination roller according to claim 21 wherein said ultrasonic bonding anvil apparatus comprises one or more ultrasonic bonding shoes and one or more ultrasonic bonding anvil hold-down shoes.

36. A combination roller according to claim 35 wherein each of said ultrasonic bonding anvil shoes and said ultrasonic bonding anvil hold-down shoes have a width, a top surface, a bottom surface, first and second edges and first and second ends; said bottom surfaces of said ultrasonic bonding anvil shoes and said ultrasonic bonding anvil hold-down shoes conforming to and fitting closely with the intermittent surface of said body portion of said combination roller.

37. A combination roller according to claim 36, wherein said first and second edges of said ultrasonic bonding anvil shoes have respective first and second flanges depending outwardly in the direction of the width of said ultrasonic bonding anvil shoes, and said first edges of said ultrasonic bonding anvil hold-down shoes having flanges depending outwardly in the direction of the width of said ultrasonic bonding anvil hold-down shoes, said flanges on said first edges of said ultrasonic bonding anvil hold-down shoe being adapted to overly, conform to, and fit closely with said flanges on the first or second edges of said ultrasonic bonding anvil shoes.

38. A combination roller according to claim 36 wherein said outer surfaces of said ultrasonic bonding anvil shoes and said ultrasonic bonding anvil hold-down shoes each define portions of a cylindrical having a radius.

39. A combination roller according to claim 38 wherein the radius of the cylindrical surface of said ultrasonic bonding anvil shoe is greater than the radius of said ultrasonic bonding anvil hold-down shoes.

40. A combination roller according to claim 38 wherein the outer surface of said ultrasonic bonding anvil shoes have recesses inwardly depending in the direction of the radius of said shoes defining an intermittent pattern on said outer surface of said ultrasonic bonding anvil shoes.

41. A combination roller according to claim 20 wherein said vacuum transfer apparatus comprises vacuum apertures in said ultrasonic bonding anvil shoes and said ultrasonic bonding anvil hold-down shoes communicating with tubular channels formed in the body portion of said combination roller between the first and second side walls and the bottom walls of said inwardly depending grooves in said body portion and the bottom surface of said ultrasonic bonding anvil shoes and said ultrasonic bonding anvil hold-down shoes.

42. A machine for cutting discrete workpieces from a first web of uncut workpieces moving at a first speed and transferring and bonding the cut workpieces to a second substrate web of material moving at a second speed, said machine comprising:
   a) a first supply apparatus delivering an uncut web of workpieces at a first component web speed;
   b) a second supply apparatus delivering a second substrate web of material at a second substrate web speed;
   c) at least one vacuum commutator;
   d) at least one ultrasonic horn having a first outer working surface;
   e) a rotary cutter having a length, said rotary cutter having a cutting edge disposed along at least a portion of said length;
   f) a combination roller having a second outer working surface, said second outer working surface of the combination roller being disposed in working relationship with said rotary cutter and with said first outer working surface of said at least one rotary ultrasonic horn, said combination roller having
      i) cutting bar anvil apparatus for engaging the cutting edge of said rotary cutter during rotation of said rotary cutter and said combination roller,
      ii) vacuum transfer apparatus communicating with said at least one vacuum commutator for receiving and holding the first uncut web of workpieces to the working surface of said combination roller for cutting of said first web into discrete workpieces between said cutting edge of said rotary cutter and said cutting bar anvil and for holding said discrete workpieces to said working surface and transferring said discrete workpieces to the second substrate web; and
      iii) ultrasonic bonding anvil apparatus cooperating with the first outer working surface of said at least one rotary ultrasonic horn to thereby create bonds bonding the cut discrete workpieces to the second substrate web; and
   f) variable speed drive apparatus driving said rotary cutter and said combination roller at said first speed for a first portion of each rotation of said rotary cutter and said combination roller at said second speed for a second portion of each rotation of said rotary cutter and said combination roller.

43. The machine according to claim 42 wherein said variable speed drive apparatus comprises a servomotor and servomotor controller for driving said roller at or near
   a) said first component web speed for a first fraction of each rotation of said roller;
   b) a first temporary speed different from said first component web speed and said second substrate web speed for a second fraction of each rotation of said roller;
   c) said second substrate web speed for a third fraction of each rotation of said roller; and
   d) a second temporary speed different from said first component web speed and said second substrate web speed for a fourth fraction of each rotation of said roller.

44. The machine according to claim 42 wherein said roller comprises a body portion having an outer surface and a shaft, said body portion outer surface defining an intermittent surface, said body portion having grooves which extend over a portion of the length of said body portion, said grooves depending inwardly from said intermittent surface of the body portion toward said central shaft, each of said grooves defining first and second side walls and a bottom wall.

45. The machine according to claim 44 wherein said body portion is separated from said shaft portion and is moveably positionable along the length of said shaft portion.

46. The machine according to claim 45 wherein said body portion is split into two or more pieces longitudinally along the length of said body portion.

47. The machine according to claim 44 wherein said cutting anvil apparatus comprises a cutting anvil bar and cutting anvil bar retainer received in one of said grooves in said body portion of said roller.

48. The machine according to claim 29 wherein said cutting anvil bar extends for at least a portion of the length of said combination roller.

49. The machine according to claim 44 wherein said ultrasonic bonding anvil apparatus comprises one or more ultrasonic bonding shoes and one or more ultrasonic bonding anvil hold-down shoes affixed to the outer surface of said roller body portion.

50. The machine according to claim 49 wherein each of said ultrasonic bonding anvil shoes and said ultrasonic bonding anvil hold-down shoes have a width, a top surface, a bottom surface, first and second edges and first and second ends; said bottom surfaces of said ultrasonic bonding anvil shoes and said ultrasonic bonding anvil hold-down shoes conforming to and fitting closely with the intermittent surface of said body portion of said combination roller.

51. The machine according to claim 50, wherein said first and second edges of said ultrasonic bonding anvil shoes have respective first and second flanges depending outwardly in the direction of the width of said ultrasonic bonding anvil shoes, said first edges flanges of said ultrasonic bonding anvil hold-down shoes, said flanges on said first edges of said ultrasonic bonding anvil hold-down shoe being adapted to abut, overly, conform to, and fit closely with said flanges on the first or second edges of said ultrasonic bonding anvil shoes.

52. The machine according to claim 50 wherein said outer surfaces of said ultrasonic bonding anvil shoes and said ultrasonic bonding anvil hold-down shoes each define portions of a cylindrical having a radius.

53. The machine according to claim 52 wherein the radius of the cylindrical surface of said ultrasonic bonding anvil shoe is greater than the radius of said ultrasonic bonding anvil hold-down shoes.

54. The machine according to claim 50 wherein the outer surface of said ultrasonic bonding anvil shoes have recesses inwardly depending in the direction of the radius of said shoes thereby defining an intermittent pattern on said outer surface of said ultrasonic bonding anvil shoes.

55. The machine according to claim 43 wherein said vacuum transport apparatus comprises vacuum apertures in said ultrasonic bonding anvil shoes and said ultrasonic bonding anvil hold-down shoes communicating with tubular channels formed in the body portion of said combination roller between the first and second side walls and the bottom walls of said inwardly depending grooves in said body portion and the bottom surface of said ultrasonic bonding anvil shoes and said ultrasonic bonding anvil hold-down shoes, said tubular channels communication with said at least one vacuum commutator.

* * * * *

UNITED STATES PATENT AND TRADEMARK OFFICE
CERTIFICATE OF CORRECTION

PATENT NO. : 6,149,755  
DATED : November 21, 2000  
INVENTOR(S) : Patrick Sean McNichols et al.

Page 1 of 1

It is certified that error appears in the above-identified patent and that said Letters Patent is hereby corrected as shown below:

Title page,  
Item [56], column 2, line 15, delete "7,863,542", and substitute -- 4,863,542 --.

Column 2,  
Line 58, after the word "which", delete "to".

Column 7,  
Line 28, delete "4308", and substitute -- 430B --.

Column 8,  
Line 58, delete "go".

Column 15,  
Line 2, delete "as".

Column 16,  
Line 62, delete "on-linear", and substitute -- non-linear --.  
Line 40, delete "1" and insert -- 3 --.

Signed and Sealed this

Nineteenth Day of March, 2002

Attest:

JAMES E. ROGAN  
*Director of the United States Patent and Trademark Office*

*Attesting Officer*